United States Patent
Matsuo et al.

(10) Patent No.: US 7,323,188 B2
(45) Date of Patent: Jan. 29, 2008

(54) COMPOSITION FOR CONTROLLING HARMFUL BIO-ORGANISMS AND METHOD FOR CONTROLLING HARMFUL BIO-ORGANISMS USING THE SAME

(75) Inventors: Norifusa Matsuo, Shiga (JP); Shigeru Mitani, Shiga (JP); Satoshi Araki, Shiga (JP); Yasuko Takii, Shiga (JP); Tomona Yamaguchi, Shiga (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 11/185,673

(22) Filed: Jul. 21, 2005

(65) Prior Publication Data

US 2005/0255171 A1  Nov. 17, 2005

Related U.S. Application Data

(62) Division of application No. 10/026,700, filed on Dec. 27, 2001, now Pat. No. 7,001,605, which is a division of application No. 09/403,368, filed as application No. PCT/JP98/01889 on Apr. 23, 1998, now Pat. No. 6,375,965.

(30) Foreign Application Priority Data

| Apr. 25, 1997 | (JP) | P. 9-123382 |
| Jun. 30, 1997 | (JP) | P. 9-190494 |
| Jul. 11, 1997 | (JP) | P. 9-202575 |
| Aug. 8, 1997 | (JP) | P. 9-227113 |
| Aug. 19, 1997 | (JP) | P. 9-238973 |

(51) Int. Cl.
  *A01N 25/32* (2006.01)

(52) U.S. Cl. ............ 424/406; 424/405; 424/630; 424/633; 424/635; 514/269; 514/398; 514/459; 514/471; 514/538; 514/539

(58) Field of Classification Search ............ None
See application file for complete search history.

(56) References Cited

U.S. PATENT DOCUMENTS

| 4,075,324 A | | 2/1978 | Thizy et al. |
| 4,995,898 A | * | 2/1991 | Nasu et al. ............ 514/227.8 |
| 5,206,228 A | | 4/1993 | Collins |
| 6,030,924 A | * | 2/2000 | Mayer et al. ............ 504/134 |

FOREIGN PATENT DOCUMENTS

| EP | 0 298 196 | 1/1989 |
| EP | 0 337 103 | 10/1989 |
| JP | 03011003 | 1/1991 |

* cited by examiner

*Primary Examiner*—Neil S. Levy
(74) *Attorney, Agent, or Firm*—Sughrue Mion, Pllc.

(57) ABSTRACT

A composition for controlling harmful bio-organisms comprising (a) at least one imidazole compound represented by formula (I):

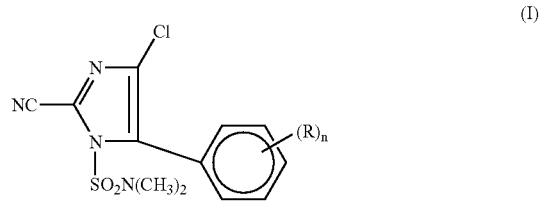

wherein R represents a lower alkyl group or a lower alkoxy group; and n represents an integer of 1 to 5, as an active ingredient, and (b) at least one inorganic phosphorus compound and/or at least one fungicide for Phycomycetes as an active ingredient or (c) a spreader as an activity-enhancing ingredient, and a method for controlling harmful bio-organisms comprising applying the composition for controlling harmful bio-organisms onto harmful bio-organisms.

3 Claims, No Drawings

COMPOSITION FOR CONTROLLING HARMFUL BIO-ORGANISMS AND METHOD FOR CONTROLLING HARMFUL BIO-ORGANISMS USING THE SAME

This is a divisional application of U.S. application Ser. No. 10/026,700, filed Dec. 27, 2001, now U.S. Pat. No. 7,001,605 which in turn is a divisional application of U.S. application Ser. No. 09/403,368 filed Oct. 21, 1999, now U.S. Pat. No. 6,375,965 as the national stage application under 37 C.F.R. § 371 of PCT/JP98/01889 filed Apr. 23, 1988. The entire disclosures of the prior applications, application numbers U.S. application Ser. Nos. 10/026,700, 09/403,368, and PCT/JP98/01889 are hereby incorporated by reference.

TECHNICAL FIELD

This invention relates to a composition having markedly enhanced controlling effects on harmful bio-organisms, especially curative and/or preventive effects on plant diseases, and are useful in agriculture and horticulture; a method for controlling harmful bio-organisms using the composition; and a method for enhancing the harmful bio-organism controlling effects of a harmful bio-organism controlling agent.

BACKGROUND ART

With reference to a combination of active ingredients (a) and (b) used in the present invention (hereinafter described), EP Patent No. 298196 teaches that the imidazole compound used in the present invention as active ingredient (a) is useful as a harmful bio-organism controlling agent, referring to the possibility of using the compound in combination with other fungicides if desired. EP Patent No. 298196 adds that a combined use of an imidazole compound structurally similar to the imidazole compound used in the present invention as active ingredient (a) with other fungicides, such as cyanoacetamide compounds (e.g., 1-(2-cyano-2-methoxyiminoacetyl)-3-ethylurea) and organic chlorine compounds (e.g., tetrachloroisophthalonitrile), brings about enhanced effects. Furthermore, EP Patent No. 337103 discloses a harmful bio-organism controlling agent containing at least one imidazole compound structurally similar to the imidazole compound used in the present invention as an active ingredient and at least one active ingredient selected from a cyanoacetamide compound, an organic chlorine compound (including tetrachloroisophthalonitrile), a phenylamide compound (including methyl N-(2-methoxyacetyl)-N-(2,6-xylyl)-DL-alaninate), a cinnamic acid compound, a copper compound, and an organophosphorus compound (including Fosetyl-Aluminum).

Reviewing these patents in view of the present invention, they do not describe nor suggest a combination of the imidazole compound as active ingredient (a) and an inorganic phosphorus compound, a β-methoxyacrylate compound or an oxazolidinedione compound. Neither do they describe nor suggest the pronouncedly excellent controlling effects which may be possessed by a composition comprising the imidazole compound as one active ingredient and at least one member selected from the group consisting of a cyanoacetamide compound, an organic chlorine compound, a phenylamide compound, a cinnamic acid compound, a copper compound, and an organophosphorus compound as the other active ingredient.

With respect to a combination of active ingredient (a) and activity-enhancing ingredient (c) (hereinafter described), EP Patent No. 298196 describes usefulness of the imidazole compound of the present invention as a harmful bio-organism controlling agent, teaching that this compound can be formulated into various forms together with adjuvants. JP-A-Heisei-3-11003 (the term "JP-A" as used herein means an "unexamined published Japanese patent application") discloses a method for controlling harmful bio-organisms comprising applying an aqueous dispersion containing at least one of the imidazole compounds of the present invention and a sorbitan higher fatty acid ester surface active agent.

The imidazole compound represented by formula (I) and many other conventional harmful bio-organism controlling agents have their several characteristics in the controlling effects. Some produce insufficient effects on some harmful bio-organisms, or some are less effective in curing than in prevention, or some have relatively short duration in residual effect. Therefore, cases are sometimes met with in which their controlling effects on harmful bio-organisms are insufficient in practice in some uses. Further, although the imidazole compound of formula (I) exhibits excellent fungicidal effects on Phycomycetes, it tends to fail to produce sufficient curative and/or preventive effects depending on the situation of the development of a disease. From this aspect, too, enhancement has been desired.

On the other hand, in practical application of a harmful bio-organism controlling agent comprising the imidazole compound of formula (I), it is desirable to minimize the amount of the compound to be used for cost saving while trying to control a plurality of harmful bio-organisms different in kind, the time of disease breakout or the time of occurrence as much as possible. Further, while the harmful bio-organism controlling agent containing the imidazole compound of formula (I) as an active ingredient is particularly excellent in preventive effect, it has been-demanded to enhance its curative effect.

DISCLOSURE OF THE INVENTION

The inventors of the present invention have studied in order to settle the above-mentioned problems and have found as a result that a combined use of the imidazole compound of formula (I) as active ingredient (a) and a specific compound as active ingredient (b) produces unexpected results such that the respective amounts of the compounds can be reduced or the respective control spectra are broadened as compared with their individual use. They have also found that a combined use of active ingredient (a) with activity-enhancing ingredient (c) brings about marked enhancement in controlling effect, particularly curative effect, as compared with the use of active ingredient (a) alone, thereby making it possible to reduce the amount of active ingredient (a) The present invention has been reached based on these findings.

The present invention relates to a composition for controlling harmful bio-organisms comprising (a) at least one imidazole compound represented by formula (I):

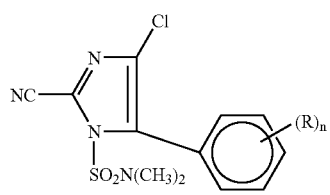

wherein R represents a lower alkyl group or a lower alkoxy group; and n represents an integer of 1 to 5, as an active ingredient, and (b) at least one inorganic phosphorus compound and/or at least one fungicide for Phycomycetes as an active ingredient or (c) a spreader as an activity-enhancing ingredient.

BEST MODE FOR PRACTICING INVENTION

In formula (I), the lower alkyl group or the alkyl moiety of the lower alkoxy group as represented by R includes an alkyl group having 1 to 6 carbon atoms, such as methyl, ethyl, propyl, butyl, pentyl or hexyl, which may have either a straight chain or a branched chain. When n is 2 or greater, the plural Rs may be the same or different.

The imidazole compounds represented by formula (I) include the following compounds:

4-chloro-2-cyano-1-dimethylsulfamoyl-5-(4-methylphenyl)imidazole (Compound No. 1);

4-chloro-2-cyano-1-dimethylsulfamoyl-5-(4-methoxyphenyl)imidazole (Compound No. 2);

4-chloro-2-cyano-1-dimethylsulfamoyl-5-(4-ethylphenyl)imidazole (Compound No. 3); and 4-chloro-2-cyano-1-dimethylsulfamoyl-5-(3-methyl-4-methoxyphenyl)imidazole (Compound No. 4).

The imidazole compounds of formula (I) can be prepared by known processes disclosed, e.g., in EP Patent No. 298196 or EP-A-705823.

The inorganic phosphorus compounds as active ingredient (b) include phosphoric acid, phosphorous acid, hypophosphorous acid, condensed phosphoric acid, condensed phosphorous acid, and salts thereof. The salts include those with light metals (specific gravity: less than 4), such as alkali metals, alkaline-earth meals, aluminum, etc.; heavy metals (specific gravity: 4 or more), such as zinc, copper, nickel, manganese, etc.; and substituted or unsubstituted ammonium salts.

Salts of phosphoric acid include primary phosphates (e.g., sodium dihydrogenphosphate, potassium dihydogenphosphate, aluminum dihydrogenphosphate, ammonium dihydrogenphosphate, calcium dihydrogenphosphate), secondary phosphates (e.g., disodium hydrogenphosphate, dipotassium hydrogenphosphate, diammonium hydrogenphosphate, dimagnesium hydrogenphosphate), and tertiary phosphates (e.g., trisodium phosphate, tripotassium phosphate, zinc phosphate, aluminum phosphate, ammonium phosphate, ammonium magnesium phosphate, magnesium phosphate, calcium phosphate).

Salts of phosphorous acid include primary or secondary phosphites (e.g., sodium primary or secondary phosphite, potassium primary or secondary phosphite, calcium primary or secondary phosphite).

Salts of hypophosphorous acid include sodium hypophosphite, barium hypophosphite, and calcium hypophosphite.

Condensed phosphoric acids and salts thereof include polyphosphoric acids (e.g., pyrophosphoric acid), and polyphosphates (e.g., sodium pyrophosphate, calcium pyrophosphate, disodium dihydrogenpyrophosphate).

Condensed phosphorous acids and salts thereof include polymetaphosphoric acids (e.g., trimetaphosphoric acid, tetrametaphosphoric acid), and polymetaphosphates (e.g., sodium trimetaphosphate, sodium tetrametaphosphate, sodium hexametaphosphate).

The fungicides for Phycomycetes which can be used as active ingredient (b) include:

β-methoxyacrylate Compounds (e.g., methyl (E)-2-{2-[6-(2-cyanophenoxy)pyrimidin-4-yloxy]phenyl}-3-methoxyacrylate, methyl (E)-methoxyimino[α-(o-tolyloxy)-O-tolyl]acetate);

Oxazolidinedione Compounds (e.g., 3-anilino-5-methyl-5-(4-phenoxyphenyl)-1,3-oxazolidine-2,4-dione);

Cyanoacetamide Compounds (e.g., 1-(2-cyano-2-methoxyiminoacetyl)-3-ethylurea (common name: Cymoxanil));

Organic Chlorine Compounds (e.g., tetrachloroisophthalonitrile (common name: Chlorothalonil), pentachloronitrobenzene (common name: Quintozen));

Phenylamide Compounds (e.g., methyl N-(2-methoxyacetyl)-N-(2,6-xylyl)-DL-alaninate (common name: Metalaxyl), 2-methoxy-N-(2-oxo-1,3-oxazolidin-3-yl)aceto-2',6'-xylidide (common name: Oxadixyl), (±)-α-2-chloro-N-(2,6-xylylacetamide)-γ-butyrolactone (common name: Ofurace), methyl N-phenylacetyl-N-(2,6-xylyl)-DL-alaninate (common name: Benalaxyl), methyl N-(2-furoyl)-N-(2,6-xylyl)-DL-alaninate (common name: Furalaxyl), (±)-α-[N-(3-chlorophenyl)cyclopropanecarboxamide]-γ-butyrolactone (common name: Cyprofuram));

Cinnamic Acid Compounds (e.g., (E,Z)-4-[(3-(4-chlorophenyl)-3-(3,4-dimethoxyphenyl)acryloyl]morpholine (common name: Dimethomorph));

Copper Compounds (e.g., organic or inorganic copper fungicides); and

Organophosphorus Compounds (e.g., aluminum tris(ethyl phosphonate) (common name: Fosetyl-aluminum), O-2,6-dichloro-p-tolyl-O,O-dimethyl phosphorothioate (common name: Tolclofosmethyl), (R,S)-S-(R,S)-sec-butyl-O-ethyl-2-oxo-2-thiazolidinyl phosphonothioate, S-benzyl diisopropyl phosphorothioate (common name: Iprobenfos), O-ethyl diphenyl phosphorodithioate (common name: Edifenphos), ethyl 2-diethoxythiophosphoryloxy-5-methylpyrazolo(1,5-a)pyrimidine-6-carboxylate (common name: Pyrazophos))

Of these, (E)-2-{2-[6-(2-cyanophenoxy)pyrimidin-4-yloxy]phenyl}-3-methoxyacrylate (hereinafter referred to as "compound (a)"), methyl (E)-methoxyimino[α-(o-tolyloxy)-O-tolyl]acetate (hereinafter referred to as "compound (b)"), and 3-anilino-5-methyl-5-(4-phenoxyphenyl)-1,3-oxazolidine-2,4-dione (hereinafter referred to as "compound (c)") are described in *Brighton Crop Prot. Conf. Pests and Diseases*, pp. 435-443 (1992), ibid, pp. 403-410 (1992), and ibid, pp. 21-26 (1996), respectively.

Of the above-described organic chlorine compounds, tetrachloroisophthalonitrile is preferred. Of the phenylamide compounds, methyl N-(2-methoxyacetyl)-N-(2,6-xylyl)-DL-alaninate is preferred. Of the organophosphorus compounds, aluminum tris(ethyl phosphonate) is preferred. Of the copper compounds, an inorganic copper fungicide is preferred.

The inorganic or organic copper fungicides as referred to the above include fungicidal preparations containing chemicals (such as fungicides, etc.) other than active ingredients (a) and (b) in addition to the copper compound.

The inorganic copper fungicides include those containing copper oxysulfate as an active ingredient, such as Sanpun Bordeaux (trade name, produced by Dai-ichi Noyaku K.K. and Hokko Chemical Industry Co., Ltd.) and Sanpun Bordeaux Dust DL (trade name, produced by Dai-ichi Noyaku K.K. and Hokko Chemical Industry Co., Ltd.); those containing copper (I) oxychloride as an active ingredient, such as San Bordeaux (trade name, produced by Sankei Chemical Co., Ltd.), Deutch Bordeaux A (trade name, produced by Dai-ichi Noyaku K.K. and Hokko Chemical Industry Co., Ltd.), Do-cal Wettable Powder (trade name, produced by Yashima Chemical Industry Co., Ltd.), Do-jet (trade name, produced by Nissan Chemical Industries, Ltd.), etc.; those containing cupric hydroxide as an active ingredient, such as Kocide Bordeaux, Kocide DF, Kocide SD (trade names, all produced by Griffin), etc.; and those containing anhydrous copper (II) sulfate, such as Gandie Wettable Powder (trade name, produced by Agro-Kanesho Co., Ltd.), etc.

The fungicidal preparations containing the inorganic copper fungicide and chemicals (such as fungicides, etc.) other than ingredients (a) and (b) include a Bordeaux mixture containing basic copper calcium sulfate; copper-sulfur fungicides, such as Engei Bordeaux (trade name, produced by Sankei Chemical Co., Ltd.), etc.; copper-validamycin fungicides; copper-validamycin-fthalide fungicides; copper-pyrifenox fungicides; copper (I)-vinclozolin fungicides; copper-fthalide fungicides; copper-procymidone fungicides, such as Scletane Wettable Powder (trade name, produced by Hokko Chemical Industry Co., Ltd.); copper (I)-fosetyl wettable powders; copper-metalaxyl fungicides, such as Ridomil Copper Wettable Powder (trade name, produced by Nihon Nohyaku Co., Ltd.); iprodione copper (I) fungicides, such as Daisedo Wettable Powder (trade name, produced by Yashima Chemical Industry Co., Ltd.); iminoctadiene triacetate-copper fungicides; oxadixyl copper (I) fungicides; oxolinic acid-copper fungicides; kasugamycin-copper fungicides, such as Kasumin Bordeaux Dust 3DL (trade name, produced by Hokko Chemical Industry Co., Ltd.), Kasumin Bordeaux (trade name, produced by Dai-ichi Noyaku K.K. and Hokko Chemical Industry Co., Ltd.), etc.; dithianone copper (I) fungicides; streptomycin-copper fungicides, such as Do-Stomy Wettable Powder (trade name, produced by Nihon Nohyaku Co., Ltd.), etc.; sodium hydrogencarbonate-copper fungicides, such as G-Fine Wettable Powder (trade name, produced by Yashima Chemical Industry Co., Ltd.); and copper-organocopper fungicides, such as Oxy Bordeaux (trade name, produced by Sankyo Co., Ltd.), Kinset Wettable Powder (trade name, produced by Agro-Kanesho Co., Ltd.), Kinset Wettable Powder 80 (trade name, produced by Agro-Kanesho Co., Ltd.), etc.

Of these inorganic copper fungicides, it is particularly preferred to use those containing one or more active ingredients selected from the group consisting of cupric hydroxide, copper oxysulfate, copper oxychloride, anhydrous copper (II) sulfate, and basic copper calcium sulfate.

The organic copper fungicides include 8-hydroxyquinoline copper fungicides, such as Quinone-do Wettable Powder 40 or 80 (trade name, produced by Agro-Kanesho Co., Ltd.), Quinone-do Granules (trade name, produced by Agro-Kanesho Co., Ltd.), Quinone-do Flowable (trade name, produced by Agro-Kanesho Co., Ltd.), Oxine-copper (I) Wettable Powder (trade name, produced by Tomono Agrica Co., Ltd.), Oxine-copper (I) Wettable Powder 75 (trade name, produced by Tomono Agrica Co., Ltd.), Oxine-copper (I) Wettable Powder 80 (trade name, produced by Tomono Agrica Co., Ltd. and Nissan Chemical Industries, Ltd.), Oxine-copper (I) Flowable (trade name, produced by Tomono Agrica Co., Ltd. and Nissan Chemical Industries, Ltd.), Doquline Wettable Powder 80 (trade name, produced by Nihon Nohyaku Co., Ltd.), and Dokirin Flowable (trade name, produced by Nihon Nohyaku Co., Ltd.), etc.; copper hydroxynonylbenzenesulfonate fungicides such as Yonepon (trade name, produced by Yonezawa Kagaku K.K.), etc.; copper (II) bis(ethylenediamine)bis(dodecylbenzenesulfonate) fungicides, such as Sanyol (trade name, produced by Otsuka Chemical Co., Ltd. and Yonezawa Kagaku K.K.), etc.; and copper terephthalate fungicides.

The fungicidal preparations containing the organic copper fungicide and fungicides other than ingredients (a) and (b) include iprodione (I)-organocopper fungicides, oxolinic acid-organocopper fungicides, captan (I)-thiuram-organocopper fungicides, captan (I)-organocopper fungicides, dithianon (I)-organocopper fungicides, streptomycin-organocopper fungicides, thiabendazole (I)-organocopper fungicides, fenarimol (I)-organocopper fungicides, machine oil-organocopper fungicides, and guazatine (I) iminoctadine-organocopper fungicides.

A spreader is used as activity-enhancing ingredient (c). Examples of the spreader for use in the present invention include surface active agents (exclusive of sorbitan higher fatty acid esters), paraffin oil, animal and/or vegetable oil, and mineral oil. In general, spreaders are not definitely classified. Some of animal and/or vegetable oil, and mineral oil serve as surface active agents, and there are some spreaders called stickers that cannot be classified clearly. Any spreader that appreciably enhances the physical properties of the imidazole compound of formula (I), such as fixing properties, penetrability, spreadability, and stomatal flooding properties, to enhance the effects of the compound can be used in the present invention. Typically, the physical properties of the imidazole compound of formula (I) could be enhanced by the spreader to bring about such an effect that equal harmful bio-organism controlling effects are obtained with a lesser amount of the compound. Of the above-described spreaders preferred are surface active agents (exclusive of sorbitan higher fatty acid esters), animal and/or vegetable oil, and mineral oil. Still preferred are nonionic surface active agents (exclusive of sorbitan higher fatty acid esters), animal and/or vegetable oil, and mineral oil.

Suitable nonionic surface active agents which can be used as activity-enhancing ingredient (c) include polyoxyethylene alkyl ethers, polyoxyethylene alkylphenyl ethers, polyoxyethylene aryl ethers, polyoxyethylene glycol alkyl ethers, polyoxyethylene fatty acid esters, polyoxyethylene polyol fatty acid esters, polyoxyethylene fatty acid amides, amine N-oxides such as Aromox C/12W (trade name, produced by Akzo Chemie), polyoxyethylene alkylamines, glycerol fatty acid esters, silicone surface active agents, polyoxyethylene alkyl thioether polyphosphate surface active agents such as Reider (trade name, produced by American Trading Company), higher alcohol sulfuric acid esters, and dialkylsulfosuccinates. Among these, preferred are polyoxyethylene alkyl ethers, polyoxyethylene alkylphenyl ethers, polyoxyethylene fatty acid esters, polyoxyethylene fatty acid amides, silicone surface active agents, higher alcohol sulfuric acid esters, and dialkylsulfosuccinates. Still preferred are silicone surface active agents, polyoxyethylene alkylphenyl ethers and polyoxyethylene fatty acid esters. Silicone surface active agents, especially Dyne Amic (trade mark, produced by Setre Chemical) and KINETIC (trade mark, produced by Setre Chemical), and SILWETT L-77 (produced by Witco), and SLIPPA (produced by Interagro) are particularly preferred.

Specific examples of preferred nonionic surface active agents are listed in Table 1 below. Additionally polyoxyethylene polysilane ether (a kind of silicone surface active agents), Renex 36 (trade name, polyoxyethylene alkyl ether produced by Bayer AG), Crop Oil Extra (trade name of a polyoxyethylene alkylphenyl ether produced by Kalo, Inc.), Ortho X-77 Spreador (trade name, produced by Chevron Chemical Company), and COOP Spreader Activator (trade name, produced by Formland Industry) are also included in usable nonionic surface active agents.

TABLE 1

Nonionic Surface Active Agents

| No. | Kind | Designation | Trade Name (Manufacturer) |
|---|---|---|---|
| 1 | Polyoxyethylene alkyl ether | | Genapol LRO Fluid (Hoechst AG) |
| 2 | Polyoxyethylene alkyl ether | ethylene oxide adduct of iso-$C_{13}$ oxo alcohol | Lutensol TO 7 (BASF AG) |
| 3 | $C_{10}$ oxo alcohol + ethylene oxide | ethylene oxide adduct of $C_{10}$ oxo alcohol | Lutensol ON 60 (BASF AG) |
| 4 | Polyoxyethylene alkylphenyl ether | | AGRAL 30 (ICI Agrochemicals) |
| 5 | Polyoxyethylene alkylphenyl ether | 90% nonyl phenoxy polyethoxyethanol | AGRAL 90 (ICI Agrochemicals) |
| 6 | Polyoxyethylene alkylphenyl ether | nonirfenpl polietilenglicol eter | AGRAL PLUS (ICI Agrochemicals) |
| 7 | Polyoxyethylene alkylphenyl ether | | ARKOPAL N-100 (Hoechst AG) |
| 8 | Polyoxyethylene alkylphenyl ether | ethylene oxide condensate | Citowett (BASF AG) or CITOWETT |
| 9 | Polyoxyethylene alkylphenyl ether | | Genapol X-60 (Hoechst AG) |
| 10 | Polyoxyethylene alkylphenyl ether | ethoxylated fatty amine | Frigate ® (ISK Biotech Europe, Ltd.) |
| 11 | polyoxyethylene aryl ether | polyoxyethylene tristyrylphenyl ether | SOPROPHOR ® BSU (RHÔNE-POULENC) |
| 12 | polyoxyethylene alkylphenyl ether | polyoxyethylene octylphenyl ether | KUSARINO (Nihon Nohyaku Co., Ltd.) |
| 13 | polyoxyethylene alkylphenyl ether | | Noigen EA110 (Daiichi Kogyo Seiyaku Co., Ltd.) |

TABLE 1-continued

Nonionic Surface Active Agents

| 14 | polyoxyethylene alkylphenyl ether + lignin sulfonate | polyethylene glycol alkylphenol ether (20%) + lignin sulfonate (12%) | TOKUSEI RINO (Nihon Nohyaku Co., Ltd.) |
|---|---|---|---|
| 15 | polyoxyethylene fatty acid ester | polyoxyethylene aliphatic alcohol | RHODASURF ® 860/P (RHÔNE-POULENC) |
| 16 | polyoxyethylene fatty acid ester | polyoxyethylene soybean amino ether | D-3605 (Takemoto Oils and Fats Co., Ltd.) |
| 17 | polyoxyethylene fatty acid ester | polyoxyethylene castor oil ether | D-230 N (Takemoto Oils and Fats Co., Ltd.) |
| 18 | polyoxyethylene fatty acid ester | polyoxyethylene rape seed oil ether | D-233 N (Takemoto Oils and Fats Co., Ltd.) |
| 19 | polyoxyethylene fatty acid ester | polyoxyethylene oleyl ether | Noigen ET-120E (Daiichi Kogyo Seiyaku Co., Ltd.) |
| 20 | polyoxyethylene fatty acid ester | polyoxyethylene fatty acid ester (70%) | Spray Sticker (Nihon Nohyaku Co., Ltd.) |
| 21 | silicone surface active agent | proprietary blend, of polyalkylene oxide-modified polymethylsiloxane, nonionic emulsifiers, and methylated vegetable oils | DyneAmic (Setre Chemical) |
| 22 | silicone surface active agent | proprietary blend of polyalkylene oxide-modified polydimethylsiloxane and nonionic surface active agents | KINETIC (Setre Chemical) |
| 23 | silicone surface active agent | (No. 23) silicone polyalkylene oxide modified polydimethyl siloxane | SILWETT L-77 (Witco) |
| 24 | Silicone surface active agent (No. 23 and Linear alcohol surfactant blend) | silicone polyalkylene oxide modified polydimethyl siloxane and linear alcohol surfactant blend | SLIPPA (Interagro) Organosilicone (Silwet L-77) |
| 25 | polyoxyethylene fatty acid amide | ethylene oxide-adduct of fatty acid amide | Lutensol FSA10 (BASF AG) |

| No. | Designation | Trade Name (Manufacturer) |
|---|---|---|
| 26 | octylphenoxy polyethoxyethanol | Citowett PLUS (BASF AG) or CITOWETT PLUS |
| 27 | dilauryl ester polyethylene glycol ester solvent c.s.p. | COADJUVANT Chevron (Bayer AG) |
| 28 | polioxiester amino grass 80 g, solvente | Hi-Point (CARGIL) |
| 29 | polyoxyethylene rosin ester | Sorpol 7261 (Toho Chemical Industry Co., Ltd.) |
| 30 | diglycerin diol fatty acid ester + polyoxyethylene monomethyl ether | Sorpol 7337 (Toho Chemical Industry Co., Ltd.) |
| 31 | polyoxyethylene rosin ester | Sorpol 7445 (Toho Chemical Industry Co., Ltd.) |
| 32 | trimethylnonyl polyethoxyethanol | Surfactant WK |
| 33 | polyglycol alkylaryl ether | TREND ® (E.I. du Pont) |
| 34 | ethylene-acrylic acid copolymer emulsion | Poligen WE3 (BASF AG) |
| 35 | | Pepol AH-053 Lot. No. 2184Y (Toho Chemical Industry Co., Ltd.) |
| 36 | benceno Surfonato de sodio eter 45 | COADJUVANT TRITON ACT-M |
| 37 | Aceitte Mineral 85% | COADJUVANT ACETITE ANPLUS |

TABLE 1-continued

Nonionic Surface Active Agents

| No. | Kind | Trade Name (Manufacturer) |
|---|---|---|
| 38 | Aceitte Mineral 83% | COADJUVANT ASSIST OIL |
| 39 | linear alcohol ethoxylate 7 mols EO | Ethylan D257 |

Suitable anionic surface active agents which can be used as activity-enhancing ingredient (c) include sulfuric ester surface active agents, such as alkylsulfuric esters or salts thereof; sulfonic acid surface active agents, such as naphthylmethanesulfonates and lignin sulfonates; fatty acid salts; and fluorine-containing surface active agents, with sulfuric ester and sulfonic acid surface active agents being preferred. Examples of preferred anionic surface active agents are shown in Table 2 below.

TABLE 2

Nonionic Surface Active Agents

| No. | Kind | Designation | Trade Name (Manufacturer) |
|---|---|---|---|
| 40 | higher alcohol sulfuric acid ester | sodium higher alcohol sulfate | Monogen Y-100 ® (Daiichi Kogyo Seiyaku Co., Ltd.) |
| 41 | dialkylsulfosuccinate | sodium dialkylsulfosuccinate | New Kalgen EP-70G (Takemoto Oils & Fats Co., Ltd.) |
| 42 | " | sodium di-2-ethylhexyl-sulfosuccinate | Genopur SB 1970J (Hoechst AG) |
| 43 | | sodium oleylmethyltauride | Hostapon T Pow. H/C (Hoechst AG) |
| 44 | | alkyl diglycol ether sulfate salt based on natural fatty alcohols; $RO-(EO)_2-SO_3Na$ | Genapol LRO paste (Hoechst AG) |
| 45 | | linosulfa to de calcio 20 + 12 | COADJUVANT RINO |

Suitable cationic surface active agents which can be used as activity-enhancing ingredient (c) include dialkylammonium salts such as NEEDS (a trade mark, produced by Kao Corporation); and alkylammonium salts such as Arguard T/50 (trade name, produced by Akzo Chemical) as shown in Table 3 below.

TABLE 3

Cationic Surface Active Agents

| No. | Kind | Designation | Trade Name (Manufacturer) |
|---|---|---|---|
| 46 | dialkylammonium salt | polynaphthyl-methanesulfonate dialkyl dimethyl-ammonium polyoxyethylene fatty acid ester | NEEDS (Kao Corporation) |
| 47 | polyoxyethylene aliphatic amine | | RHODAMEEN ® (RHÔNE-POULENC) |

The animal and/or vegetable oil which can be used as activity-enhancing ingredient (c) include vegetable oil, such as corn oil, soybean oil, linseed oil, sunflower oil, cotton seed oil, and rape seed oil; and animal oil, such as beef tallow and train oil (whale oil). Alkylated (e.g., methylated) vegetable oil such as SCOIL (manufactured by MVRC) is also included. Specific examples of suitable animal and/or vegetable oil are shown in Table 4 below. Among these, alkylated vegetable oil is preferred.

TABLE 4

Animal and/or Vegetable Oil

| No. | Kind | No. | Kind (Manufacturer) |
|---|---|---|---|
| 48 | corn oil | 53 | soybean 90% emulsion |
| 49 | corn oil emulsion | 54 | soybean oil |
| 50 | corn oil emulsion | 55 | SCOIL (MVRC) |
| 51 | corn oil emulsion | 56 | linseed oil emulsion (ICI Agrochemicals) |
| 52 | soybean oil | 57 | animal oil Ethokem (Midkem Agrochemicals) |

| No. | Kind | Designation | Trade Name |
|---|---|---|---|
| 58 | coconut oil | modified coco diethanolamide/inert ingredients couplers and solubilizing agents | Seawet or SEAWET (Sea-Born Subsidiary Lane, Inc.) |

The paraffin oil which can be used as activity-enhancing ingredient (c) includes product originated animal and/or vegetable oil, product originated mineral oil (e.g., petroleum), and mixtures thereof. Specific examples are shown in Table 5 below.

TABLE 5

Paraffin Oil

| No. | Kind | Designation | Trade name (Manufacturer) |
|---|---|---|---|
| 59 | paraffin oil | | ATPLUS 411F (ICI Agrochemicals) |
| 60 | " | | ATPLUS 411F OIL (ICI Agrochemicals) |
| 61 | " | nonionic surfactant | SUN OIL ADJUVANT (Schering Agrochemicals, Ltd.) |
| 62 | " | petroleum based paraffinic oil nonionic surfactants | OLEOTAN (Biomex) |
| 63 | " | petroleum based paraffinic oil nonionic surfactants | PRIME OIL |

The mineral oil which can be used as activity-enhancing ingredient (c) include machine oil, fuel oil, and silicone oil. Examples of preferred mineral oil are shown in Table 6 below. Among these, ISHIOIL (manufactured by Ishihara Sangyo Kaisha, Ltd.) is the most preferred.

TABLE 6

Mineral Oil

| No. | Kind | Designation | Trade Name (Manufacturer) |
|---|---|---|---|
| 64 | mineral oil (machine oil) | | machine oil emulsion |

TABLE 6-continued

Mineral Oil

| No. | Kind | Designation | Trade Name (Manufacturer) |
|---|---|---|---|
| 65 | mineral oil (machine oil) | | machine oil emulsion (Toho Chemical Industry Co., Ltd.) |
| 66 | mineral oil (fuel oil) | | diesel engine oil emulsion |
| 67 | mineral oil | mineral oil (98%) + tensio activo (2%) | ISHIOIL (Ishihara Sangyo Kaisha, Ltd.) |
| 68 | " | blend of heavy range paraffin base petroleum oil, polyol fatty acid esters, and polyethoxylated derivatives | AGRI-DEX or Agri-Dex (Helena Chemical Company) |

The above-described spreaders, i.e., surface active agents (except sorbitan higher fatty acid esters), animal and/or vegetable oil, paraffin oil, mineral oil, etc.) can be combined appropriately for use as activity-enhancing ingredient (c). Combinations of two or more spreaders include vegetable oil containing surface active agents, such as Soy Dex (Helena Chemical Company) etc.; and paraffin oil containing surface active agents, such as Oleo DP 11E (E.I. du Pont), Fyzol 11E (Schering Agrochemicals), Agri Dex (Helena Chemical Co.), Atplas 411 (ICI Agrochemicals), HerbiLmax (Love Land Industries, Inc.), Competitor Crop. Oil Concentrate (Red Pancer Chemical), Actipron (Oil Co.), DASH (BASF AG), Atlas Adherb (Atlas Interlates, Ltd.), Cropspray (Tribart Farm Chemical), Agravia 11E (Wakker Chemie), Penetrator (Helena Chemical Co.), Atlus Adjuvant Oil (Atlus Interlates, Ltd.), etc. Mixed spreaders shown in Table 7 are also included.

TABLE 7

Mixed Spreaders

| No. | Designation | Trade Name |
|---|---|---|
| 69 | mineral oil + vegetable oil | mineral oil emulsion + soybean oil emulsion |
| 70 | 2-pyrrolidione + 1-octyl-2-pyrrolidione + 1-ethenyl-1-hexadecyl homopolymer + calcium dodecylbenzenesulfonate | Agrimax 3H |

As stated above, any spreader can be used in the present invention as far as it significantly enhances the physical properties of the imidazole compound of formula (I) to enhance the effects of the compound, whatever kind it belongs to. Specific examples of useful spreaders that cannot be classified into any of the above listed kinds are shown in Table 8 below. As a matter course, a composition for controlling harmful bio-organisms containing at least one imidazole compound of formula (I) as active ingredient (a) having incorporated therein the spreader usable as activity-enhancing ingredient (c) in a ratio according to the present invention is expected to exhibit similar effects.

TABLE 8

Unclassifiable Spreaders

| No. | Designation | Trade Name (Manufacturer) |
|---|---|---|
| 71 | | Adherex MR (ISK Mexico) |
| 72 | | Atlox-BI (Kao Corporation) |
| 73 | sol de olamina del acido dodecil benceno sulfuronico (33%) + solvente (aqua) estabilizante e impurezas (67%) | EXTRAVON ® 40 (Ciba-Geigy Agrochemicals, Ltd.) |
| 74 | | SUPER CORAL ADH-50 (Grupocoret) |
| 75 | | SURFATE 30 (E.I. du pont) |
| 76 | | ALBOL INEUM AK (ICI Agrochemicals) |
| 77 | | ATPLUS SL 92 (ICI Agrochemicals) |
| 78 | | Nisseki Noyaku Oil Emulsion (Nippon Oil Co., Ltd.) |
| 79 | | OLEO RUSTICA 11E (Hoechst AG) |
| 80 | | SURF OIL (Hoechst AG) |
| 81 | | ADJUVANT No. 1 (Toho Chemical Industry Co., Ltd.) |
| 82 | aceitte parafinico 81% | Ulvapron ® |
| 83 | | X2-5309 (Toray Industries, Inc.) |
| 84 | blend of alkylphenyl hydroxy-polyoxyethylene polymerized resins and fatty acids (78%) + paraffin base petroleum oil (22%) | Helena Surfix (Helena Chemical Co.) |
| 85 | | Helena Suraid (Helena Chemical Co.) |
| 86 | | COADJUVANT NATURL OIL (Stoller Chemical Co.) |
| 87 | polioxy ester amino graso 42 | COADJUVANT SP-SUPER |
| 88 | synthetic latex (45%) + primary aliphatic oxyalkylated alcohol (10%) + inert ingredients (45%) | Bond (Loveland Industries, Inc.) |
| 89 | higher alkyl pyrrolidones combined with water-insoluble polymers (pseudo cationic polymers) and surfactants | Banka (formerly ANKA) (Interagro) |
| 90 | alkoxylated amine (alkoxylated fatty amine polymer)/polysaccharide (sugar-based nonionic surfactant and buffer) blend | ARMA (Interagro) |
| 91 | modified phthalic/glycerol alkyl resin (77%) + butyl alcohol (23%) | LATRON B-1956 (Rohm & Haas Co.) |
| 92 | blend of DL-1-p-menthene (96%) + inert ingredients (4%) | LASTIC (Helena Chemical Co.) |

The above-described fungicides for Phycomycetes as active ingredient (b) characteristically have one or more of a preventive effect, a curative effect and penetrability. Some of the inorganic phosphorus compounds as active ingredient (b), which are not fungicides, possess one or more of a preventive effect, a curative effect, and penetrability similarly to the fungicides for Phycomycetes.

The term "fungicides having a preventive effect" means that the fungicides have an ability of preventing plant diseases. Examples of such fungicides include β-methoxyacrylate compounds, oxazolidinedione compounds, cyanoacetamide compounds, organic chlorine compounds, phenylamide compounds, cinnamic acid compounds, copper compounds, and organophosphorus compounds.

The term "fungicides having a curative effect" means that the fungicides can migrate through the plant body to control an invading harmful bio-organism. Examples of such fungicides include β-methoxyacrylate compounds, cyanoacetamide compounds, phenylamide compounds, cinnamic acid compounds, and organophosphorus compounds.

The term "fungicides having penetrability" means that the fungicides having an ability of penetrating through the surface of leaves into the inside. Examples of such fungicides include β-methoxyacrylate compounds, oxazolidinedione compounds, cyanoacetamide compounds, phenylamide compounds, cinnamic acid compounds, and organophosphorus compounds.

In addition to the fungicides that have been named, other fungicides for Phycomycetes having at least one of a preventive effect, a curative effect and penetrability are also expected to produce the same effects as observed in the present invention. For example, dithiocarbamate fungicides can be mentioned as an example of fungicides for Phycomycetes having only a preventive effect.

The compositions for controlling harmful bio-organisms according to the present invention which comprises at least one imidazole compound of formula (I) as active ingredient (a) and at least one inorganic phosphorus compound as active ingredient (b) are particularly suitable for agricultural and horticultural uses. Specifically, they exhibit excellent effects of controlling diseases of crop plants, such as rice blast caused by *Pyricularia oryzae*, rice sheath blight caused by *Rhizoctonia solani*, cucumber anthracnose caused by *Colletotrichum lagenarium*, cucumber powdery mildew caused by *Sphaerotheca fuliginea*, cucumber downy mildew caused by *Pseudoperonospora cubensis*, tomato late blight caused by *Phytophthora infestans*, tomato early blight caused by *Alternaria solani*, citrus melanose caused by *Diaporthe citri*, citrus common green mold caused by *Penicillium digitatum*, pear scab caused by *Venturia nashicola*, apple *Alternaria* blotch caused by *Alternaria mali*, grape downy mildew caused by *Plasmopara viticola*, gray mold caused by *Botrytis cinerea*, Sclerotial rot caused by *Sclerotinia sclerotiorum*, and disease caused by rust, etc.; and soil diseases caused by phytopathogenic fungi, such as *Fusarium, Pythium, Rhizoctonia, Verticillium*, and *Plasmodiophora*, etc. In particular, the compositions of the present invention exhibit excellent effects of controlling diseases such as potato late blight caused by *Phytophthora infestans*, sweet pepper *Phytophtora* blight caused by *Phytophthora capsici*, watermelon *Phytophthora* rot caused by *Phytophthora drechsleri*, tobacco black shank caused by *Phytophthora nicotianae* var. *nicotianae*, tomato late blight caused by *Phytophthora infestans*, cucumber or melon downy milder caused by *Pseudoperonospora cubensis*, cabbages or Chinese cabbages downy mildew caused by *Peronospora brassicae*, onion downy mildew caused by *Peronospora destructor*, onion shiroiro-eki-byo caused by *Phytophthora porri* and watermelon brown rot caused by *Phytophthora capsici*, and grapedowny mildew caused by *Plasmopara viticola* and various soil diseases caused by e.g., *Aphanomyces, Pythium*. The compositions have a prolonged residual effect and exhibit a particularly excellent curative effect. It is therefore possible to control diseases by treatment after infection. In addition, since the compositions possess a systemic activity, it is possible to control diseases of stems and foliage by soil treatment.

The compositions for controlling harmful bio-organisms according to the present invention which comprises at least one imidazole compound of formula (I) as active ingredient (a) and a fungicide for Phycomycetes as active ingredient (b) have excellent bactericidal activities when applied to crop plants, for example, fruit vegetables (e.g., cucumbers, tomatoes, eggplants, etc.); cereals (e.g., rice, wheat, etc.); seed vegetables; fruits (e.g., apples, pears, grapes, citrus, etc.); potatoes, etc., which have been infected, or suspected of being infected, with pathogenic fungi. They exhibit excellent controlling effects on diseases, such as powdery mildew, downy mildew, anthracnose, gray mold, common green mold, Sclerotial rot, scab, *Alternaria* blotch, bacterial spot, black spot, melanose, ripe rot, late blight, early blight, blast, sheath blight, damping-off, southern blight, etc. The compositions also exert excellent controlling effects on soil diseases caused by Phycomycetes, such as *Pythium*, and other plant pathogens, such as *Fusarium, Rhizoctonia, Verticillium, Plasmodiophora*, etc. The compositions have a prolonged residual effect and exhibit a particularly excellent curative effect. It is therefore possible to control diseases by treatment after infection. In addition, since the compositions possess a systemic activity, it is possible to control diseases of stems and foliage by soil treatment.

In particular, the compositions comprising at least one imidazole compound of formula (I) as active ingredient (a) and a copper compound and/or an organophosphorus compound as a fungicide for Phycomycetes as active ingredient (b) are particularly useful in agriculture and horticulture. Specifically, the compositions exhibit excellent effects of controlling diseases of crop plants, such as rice blast caused by *Pyricularia oryzae*, rice sheath blight caused by *Rhizoctonia solani*, cucumber anthracnose caused by *Colletotrichum lagenarium*, cucumber powdery mildew caused by *Sphaerotheca fuliginea*, cucumber downy mildew caused by *Pseudoperonospora cubensis*, tomato late blight caused by *Phytophthora infestans*, tomato early blight caused by *Alternaria solani*, citrus melanose caused by *Diaporthe citri*, citrus common green mold caused by *Penicillium digitatum*, pear scab caused by *Venturia nashicola*, apple *Alternaria* blotch caused by *Alternaria mali*, grape downy mildew caused by *Plasmopara viticola*, gray mold caused by *Botrytis cinerea, sclerotinia* rot caused by *Sclerotinia sclerotiorum*, rust, bacterial spot, etc.; and soil diseases caused by phytopathogenic fungi, such as *Fusarium, Pythium, Rhizoctonia, Verticillium, Plasmodiophora*, etc. In particular, the compositions of the present invention exhibit excellent effects of controlling diseases such as potato or tomato late blight caused by *Phytophthora infestans*, cucumber downy mildew caused by *Pseudoperonospora cubensis*, grape downy milder caused by *Plasmopara viticola*; and various soil diseases caused by Phycomycetes, such as *Plasmodiophora, Aphanomyces, Pythium*, etc.

The compositions of the present invention have a prolonged residual effect so that they exhibit an excellent preventive effect, and also exhibit an excellent curative effect as well. It is therefore possible to control diseases by treatment after infection. In addition, since they possess a systemic activity, it is also possible to control diseases of the stem and leaf by soil treatment.

In particular, the compositions containing a copper compound as a fungicide for Phycomycetes exhibit an excellent preventive effect, and the compositions containing an organophosphorus compound as a fungicide for Phycomycetes exhibit an excellent curative effect.

The compositions for controlling harmful bio-organisms comprising at least one imidazole compound of formula (I) as active ingredient (a) and a cyanoacetamide compound, a phenylamide compound or a cinnamic acid compound as a fungicide for Phycomycetes as active ingredient (b) exhibit excellent controlling effects on diseases caused by Phycomycetes, such as plant diseases, e.g., downy mildew of cucumbers, melons, cabbages, Chinese cabbages, onions, pumpkins, and grapes; late blight of potatoes, red peppers, sweet peppers, watermelons, pumpkins, tobaccos, and tomatoes; onion shiroiro-eki-byo; watermelon brown rot; soil diseases caused by plant pathogenic fungi, such as *Pythium*, etc. It also has excellent controlling effects on diseases caused by *Plasmodiophora*.

The compositions for controlling harmful bio-organisms comprising at least one imidazole compound of formula (I) as active ingredient (a) and a β-methoxyacrylate compound, an oxazolidinedione compound or an organic chlorine compound as a fungicide for Phycomycetes as active ingredient (b) exhibit excellent controlling effects against diseases caused by Phycomycetes, such as plant diseases, e.g., rice blast; rice sheath blight; cucumber anthracnose; downy mildew of cucumbers, melons, cabbages, Chinese cabbages, onions, pumpkins, and grapes; powdery mildew of wheat, barley and cucumbers; late blight of potatoes, red peppers, sweet peppers, watermelons, pumpkins, tobaccos, and tomatoes; wheat speckled leaf blotch; tomato early blight; citrus melanose; citrus common green mold; pear scab; apple *Alternaria* blotch; onion shiroiro-eki-byo; watermelon brown rot; various diseases such as gray mold, sclerotial rot, rust, and bacterial spot; various soil diseases caused by plant pathogenic fungi, etc., such as *Fusarium, Pythium, Rhizoctonia, Verticillium*, etc. It also has excellent controlling effects on diseases caused by *Plasmodiophora*. The compositions show particularly excellent controlling effects on diseases such as *Phytophthora* rot of potatoes, red peppers, sweet peppers, watermelons, pumpkins, tobaccos, tomatoes, etc.; and downy mildew of cucumbers, melons, cabbages, Chinese cabbages, onions, pumpkins, grapes, etc.

Further, the compositions comprising active ingredients (a) and (b) of the present invention show an excellent controlling effect against agriculturally and horticulturally harmful insects, such as planthoppers (*Delphacidae*), diamondback moth (*Plutella xylostella*), green rice leafhopper (*Nephotettix cincticeps*), adzuki bean weevil (*Callosobruchus chinensis*), common cutworm (*Spodoptera litura*), green peach aphid (*Myzus persicae*), etc.; mites, such as two-spotted spider mite (*Tetranychus urticae*), carmine spider mite (*Tetranychus cinnabarinus*), citrus red mite (*Panonychus citri*), etc.; and nematodes, such as southern root-knot nematode (*Meloidogyne incognita*), etc.

The compositions for controlling harmful bio-organisms comprising active ingredient (a) and activity-enhancing ingredient (c) of the present invention are particularly suitable for agricultural and horticultural uses. The harmful bio-organisms which can be controlled by the compositions include plant pathogenic fungi causing plant diseases, such as rice blast; rice sheath blight; cucumber anthracnose; cucumber powdery mildew; downy milder of cucumber, melon, cabbage, Chinese cabbage, onion and grape; late blight of potato, red pepper, sweet pepper, watermelon, pumpkin, tobacco; tomato *Phytophthora* rot; tomato early blight; citrus melanose; citrus common green mold; pear scab; apple *Alternaria* blotch; various plant diseases such as gray mold, sclerotial rot, rust, etc.; soil borne pathogenic fungi causing various plant diseases, such as *Fusarium, Pythium, Rhizoctonia, Verticillium, Plasmodiophora*, etc.; insects, such as planthoppers, diamondback moth, green rice leafhopper, adzuki bean weevil, common cutworm, green peach aphid, etc.; mites, such as two-spotted spider mite, carmine spider mite, citrus red mite, etc.; and nematodes, such as southern root-knot nematode, etc. More specifically, they are effective on *Phytophthora* rot of potatoes, red peppers, sweet peppers, watermelons, pumpkins, tobaccos, and tomatoes and downy mildew of cucumbers, melons, cabbages, Chinese cabbages, onions, pumpkins, and grapes. The compositions comprising active ingredient (a) and activity-enhancing ingredient (c) have a prolonged residual effect and exhibit not only an excellent preventive effect but an excellent curative effect. It is therefore possible to control diseases by treatment after infection.

The active ingredients, inclusive of other pesticides hereinafter described as well as active ingredients (a) and (b), and activity-enhancing ingredient (c) which constitute the compositions for controlling harmful bio-organisms of the present invention can be formulated into a variety of forms, such as emulsifiable concentrates, dusts, wettable powders, aqueous solutions, granules, suspension concentrates, etc., together with various adjuvants, as in conventional agricultural preparations. Active ingredient (a) (the imidazole compound of formula (I)), active ingredient (b) and other specific compounds may be mixed and formulated, or each of them may be separately formulated and then mixed together. Upon use, the preparation may be used as such or as diluted with an appropriate diluent, e.g., water, to a predetermined concentration.

Examples of the adjuvants which can be used include carriers, emulsifying agents, suspending agents, thickeners, stabilizers; dispersants, spreaders except those used as activity-enhancing ingredient (c), surface active agents, wetting agents, penetrating agents, antifreezing agents, antifoaming agents, etc. These adjuvants are added appropriately according to necessity.

The carriers are classified into solid carriers and liquid carriers. The solid carriers include animal and vegetable powders (e.g., starch, sugar, cellulose powders, cyclodextrin, activated charcoal, soybean powders, wheat powders, chaff powders, wood powders, fish powders, powdery milk, etc.); and mineral powders (e.g., talc, kaolin, bentonite, bentonite-alkylamine complexes, calcium carbonate, calcium sulfate, sodium hydrogencarbonate, zeolite, diatomaceous earth, white carbon, clay, alumina, silica, sulfur powder, slaked lime, etc.). Examples of the liquid carriers include water, vegetable oils (e.g., soybean oil, cotton seed oil), animal oils (e.g., beef tallow, train oil, etc.), alcohols (e.g., ethyl alcohol, ethylene glycol, etc.), ketones (e.g., acetone, methyl ethyl ketone, methyl isobutyl ketone, isophorone, etc.), ethers (e.g., dioxane, tetrahydrofuran, etc.), aliphatic hydrocarbons (e.g., kerosene, lamp oil, liquid paraffin, etc.), aromatic hydrocarbons (e.g., toluene, xylene, trimethylbenzene, tetramethylbenzene, cyclohexane, solvent naphtha, etc.), halogenated hydrocarbons (e.g., chloroform, chlorobenzene, etc.), acid amides (e.g., dimethylformamide, etc.), esters (e.g., ethyl acetate, fatty acid glycerine esters, etc.), nitriles (e.g., acetonitrile, etc.), sulfur-containing compounds (e.g., dimethyl sulfoxide, etc.), N-methyl-2-pyrrolidone, N,N-dimethylformamide and so on. The spreaders (except those used as activity-enhancing ingredient (c)) or surface active agents include polyoxyethylene sorbitan fatty acid esters.

In the compositions comprising at least one imidazole compound of formula (I) as active ingredient (a) and at least one inorganic phosphorus compound as active ingredient (b), the weight ratio of (a) to (b) is usually 1:300 to 300:1, preferably 1:100 to 100:1, still preferably 1:50 to 5:1, most preferably 1:50 to 1:10.

In the compositions comprising at least one imidazole compound of formula (I) as active ingredient (a) and at least one fungicide for Phycomycetes as active ingredient (b), the weight ratio of (a) to (b) is usually 1:10000 to 10000:1, preferably 1:1000 to 10000:1, still preferably 1:100 to 1000:1. Especially in the compositions containing at least one imidazole compound of formula (I) as active ingredient (a) and at least one cyanoacetamide compound as active ingredient (b) (fungicide for phycomycetes) is preferably 1:300 to 5:1. Where, in particular, copper compounds and/or organophosphorus compounds are used as active ingredient (b) (fungicide for Phycomycetes), the weight ratio of (a) to (b) is usually 1:2000 to 2000:1, preferably 1:300 to 300:1, still preferably 1:100 to 100:1, particularly preferably 1:50 to 5:1.

In the compositions containing active ingredient (a) and activity-enhancing ingredient (c), the weight ratio of (a) to (c) is usually 1:5000 to 2000:1, preferably 0.05:99.95 to 90:10, still preferably 0.2:99.8 to 80:20.

A method for controlling harmful bio-organisms comprising applying the compositions for controlling harmful bio-organisms of the prevent invention is also included under the scope of the present invention.

In using the compositions for controlling harmful bio-organisms comprising at least one imidazole compound of formula (I) as active ingredient (a) and at least one inorganic phosphorus compound as active ingredient (b), the concentrations of use of the active ingredients (a) and (b) cannot be generally defined because they vary depending on, for example, the crop plant to be treated, the method of treatment, the form of the preparation, and the amount of the preparation to be applied. For example, the imidazole compound of formula (I) and the inorganic phosphorus compound are used in concentrations of 1 to 1000 ppm and 1 to 5000 ppm, respectively, in foliar treatment, and 10 to 10,000 g/ha and 10 to 50,000 g/ha, respectively, in soil treatment.

In using the compositions for controlling harmful bio-organisms comprising at least one imidazole compound of formula (I) as active ingredient (a) and at least one fungicide for Phycomycetes selected from the group consisting of a β-methoxyacrylate compound, an oxazolidinedione compound, a cyanoacetamide compound, an organic chlorine compound, a phenylamide compound, and a cinnamic acid compound as active ingredient (b), the concentrations of use of the active ingredients cannot be generally defined because they vary depending on the kind of the fungicide used, the crop plant to be treated, the method of treatment, the form of the preparation, the amount of the preparation to be applied, the timing of treatment, and the kind of the harmful fungi to be controlled. For foliar treatment, for example, the imidazole compound of formula (I) and the fungicide are used in concentrations of 0.01 to 1000 ppm and 0.01 to 1000 ppm, respectively, preferably 0.1 to 500 ppm and 0.1 to 500 ppm, respectively.

In using the compositions for controlling harmful bio-organisms comprising at least one imidazole compound of formula (I) as active ingredient (a) and a copper compound and/or an organophosphorus compound as active ingredient (b), the concentrations of use of the active ingredients cannot be generally defined because they vary depending on, for example, the kind of the fungicide used, the crop plant to be treated, the method of treatment, the form of the preparation, the amount of the preparation to be applied, the timing of treatment, and the kind of the harmful fungi to be controlled. For example, the imidazole compound of formula (I) and the fungicide are used in concentrations of 0.01 to 1000 ppm and 1 to 5000 ppm, respectively, in foliar treatment and 10 to 10,000 g/ha and 10 to 50,000 g/ha, respectively, in soil treatment.

In using the compositions comprising active ingredient (a) and activity-enhancing ingredient (c), the concentrations of use of these ingredients cannot be generally defined because they vary depending on, for example, the crop plant to be treated, the method of treatment, the form of the preparation, and the amount of the preparation to be applied. For example, active ingredient (a) and activity-enhancing ingredient (c) are used in concentrations of 0.1 to 10,000 ppm and 0.01 to 50 ppm, respectively, in foliar treatment and 0.01 to 100 kg/ha and 0.1 to 0-0.5 kg/ha, respectively, in soil treatment.

The compositions comprising active ingredients (a) and (b) can be used as a mixture or in combination with, for example, other pesticides, fertilizers, and safeners, to exhibit enhanced effects and actions. Useful pesticides include bactericides except those used as active ingredients (a) and (b), fungicides, insecticides, acaricides, nematicides, antiviral agents, attaractants, herbicides, and plant growth regulators. In particular, mixtures or combinations of the compositions for controlling harmful bio-organisms of the present invention and one or more active ingredients of fungicides other than those used as active ingredients (a) and (b) can enjoy enhancements, for example, in terms of the range of controllable harmful bio-organisms, the timing of treatment, and the controlling activity on harmful bio-organisms. The imidazole compound of formula (I) as active ingredient (a), the inorganic phosphorus compound and/or fungicide for Phycomycetes as active ingredient (b), and the active ingredient(s) of fungicides other than those used as active ingredients (a) and (b) can be separately formulated and mixed together on use, or one or at least two of them can be mixed and formulated into a single preparation.

Where at least one imidazole compound of formula (I) as active ingredient (a) is combined with at least one of the inorganic phosphorus compound and/or at least one of the fungicides for phycomycetes as active ingredient (b), a composition prepared immediately before use manifests further enhanced controlling effects over a previously prepared composition. Therefore, it is convenient that a composition containing active ingredient (a) and, if desired, various adjuvants and a composition containing active ingredient (b) and, if desired, various adjuvants are separately packed and supplied as a two-pack preparation. For example, active ingredient (a) and active ingredient (b) can be dissolved in respective liquid carriers and packed separately, or active ingredient (a) and a mixture of active ingredient (b) and other fungicides are dissolved in respective liquid carriers and packed separately.

In the harmful bio-organism controlling method using the compositions comprising active ingredient (a) and activity-enhancing ingredient (c), the compositions can be used as a mixture with the above-described other pesticides, which can bring about further enhanced effects. Typical examples of useful other pesticides include azole compounds such as Triflumizole (common name), etc.; quinoxaline compounds such as Quinomethionate (common name), etc.; benzimidazole compounds such as Benomyl (common name), etc.; pyridinamine compounds such as Fluazinam (common name), etc.; sulfenic acid compounds such as Dichlofluanid (common name), etc.; isoxazole compounds such as Hydroxyisoxazole (common name), etc.; dicarboxyimide compounds such as Procymidone (common name), etc.;

benzanilide compounds such as Flutolanil (common name) etc.; and benzamide compounds such as (R,S)-4-chloro-N-[cyano(ethoxymethyl]benzamide, etc.

Preferred embodiments of the compositions for controlling harmful bio-organisms according to the present invention which comprise active ingredients (a) and (b) are shown below for illustrative purposes only but not for limitation.

(1) The compositions for controlling harmful bio-organisms wherein at least one inorganic phosphorus compound and/or at least one fungicide for Phycomycetes have a preventive effect.

(2) The compositions for controlling harmful bio-organisms wherein at least one inorganic phosphorus compound and/or at least one fungicide for Phycomycetes have a curative effect.

(3) The compositions for controlling harmful bio-organisms wherein at least one inorganic phosphorus compound and/or at least one fungicide for Phycomycetes have penetrability.

(4) The compositions for controlling harmful bio-organisms wherein at least one inorganic phosphorus compound and/or at least one fungicide for Phycomycetes have a preventive effect and a curative effect.

(5) The compositions for controlling harmful bio-organisms wherein at least one inorganic phosphorus compound and/or at least one fungicide for Phycomycetes have a preventive effect and penetrability.

(6). The compositions for controlling harmful bio-organisms wherein at least one inorganic phosphorus compound and/or at least one fungicide for Phycomycetes have a curative effect and penetrability.

(7) The compositions for controlling harmful bio-organisms wherein at least one inorganic phosphorus compound and/or at least one fungicide for Phycomycetes have a preventive effect, a curative effect and penetrability.

(8) The compositions for controlling harmful bio-organisms wherein active ingredient (b) is at least one inorganic phosphorus compound.

(9) The compositions for controlling harmful bio-organisms wherein active ingredient (b) is at least one fungicide for Phycomycetes.

(10) The compositions for controlling harmful bio-organisms according to (9) above, wherein the fungicide for Phycomycetes is a compound selected from the group consisting of a β-methoxyacrylate compound, an oxazolidinedione compound, a cyanoacetamide compound, an organic chlorine compound, a phenylamide compound, a cinnamic acid compound, a copper compound, and an organophosphorus compound.

(11) The compositions for controlling harmful bio-organisms according to (9) above, wherein the fungicide for Phycomycetes is a β-methoxyacrylate compound and/or an oxazolidinedione compound.

(12) The compositions for controlling harmful bio-organisms according to (9) above, wherein the fungicide for Phycomycetes is a compound selected from the group consisting of a cyanoacetamide compound, an organic chlorine compound, a phenylamide compound, a cinnamic acid compound, a copper compound, and an organophosphorus compound.

(13) The compositions for controlling harmful bio-organisms according to (9), (10) or (11) above, wherein the fungicide for Phycomycetes is a β-methoxyacrylate compound.

(14) The compositions for controlling harmful bio-organisms according to (13), wherein the β-methoxyacrylate compound is methyl (E)-2-{2-[6-(2-cyanophenoxy)pyrimidin-4-yloxy]phenyl}-3-methoxyacrylate or methyl (E)-methoxyimino[α-(o-tolyloxy)-O-tolyl]acetate.

(15) The compositions for controlling harmful bio-organisms according to (9), (10) or (11), wherein the fungicide for Phycomycetes is an oxazolidinedione compound.

(16) The compositions for controlling harmful bio-organisms according to (15), wherein the fungicide for Phycomycetes is 3-anilino-5-methyl-5-(4-phenoxyphenyl)-1,3-oxazolidine-2,4-dione.

(17) The compositions for controlling harmful bio-organisms according to (9), (10) or (12), wherein the fungicide for Phycomycetes is a cyanoacetamide compound.

(18) The compositions for controlling harmful bio-organisms according to (17), wherein the cyanoacetamide compound is 1-(2-cyano-2-methoxyiminoacetyl)-3-ethylurea.

(19) The compositions for controlling harmful bio-organisms according to (9), (i) or (12), wherein the fungicide for Phycomycetes is an organic chlorine compound.

(20) The compositions for controlling harmful bio-organisms according to (19), wherein the organic chlorine compound is tetrachloroisophthalonitrile or pentachloronitrobenzene.

(21) The compositions for controlling harmful bio-organisms according to (19), wherein the organic chlorine compound is tetrachloroisophthalonitrile.

(22) The compositions for controlling harmful bio-organisms according to (9), (10) or (12), wherein the fungicide for Phycomycetes is a phenylamide compound.

(23) The compositions for controlling harmful bio-organisms according to (22), wherein the phenylamide compound is at least one compound selected from the group consisting of methyl N-(2-methoxyacetyl)-N-(2,6-xylyl)-DL-alaninate, 2-methoxy-N-(2-oxo-1,3-oxazolidin-3-yl)aceto-2',6'-xylidide, (±)-α-2-chloro-N-(2,6-xylylacetamide)-γ-butyrolactone, methyl N-phenylacetyl-N-(2,6-xylyl)-DL-alaninate, methyl N-(2-furoyl)-N-(2,6-xylyl)-DL-alaninate, and (±)-α-[N-(3-chlorophenyl)-cyclopropanecarboxamide]-γ-butyrolactone.

(24) The compositions for controlling harmful bio-organisms according to (22), wherein the phenylamide compound is methyl N-(2-methoxyacetyl)-N-(2,6-xylyl)-DL-alaninate.

(25) The compositions for controlling harmful bio-organisms according to (9), (10) or (12), wherein the fungicide for Phycomycetes is a cinnamic acid compound.

(26) The compositions for controlling harmful bio-organisms according to (25), wherein the cinnamic acid compound is (E,Z)-4-[3-(4-chlorophenyl)-3-(3,4-dimethoxyphenyl)acryloyl]morpholine.

(27) The compositions for controlling harmful bio-organisms according to (9), (10) or (12), wherein the fungicide for Phycomycetes is a copper compound and/or an organophosphorus compound.

(28) The compositions for controlling harmful bio-organisms according to (27), wherein the copper compound is an inorganic copper fungicide and/or an organic copper fungicide.

(29) The compositions for controlling harmful bio-organisms according to (28), wherein the active ingredient of the inorganic copper fungicide is at least one member selected from the group consisting of cupric hydroxide, copper oxysulfate, copper oxychloride, anhydrous copper (II) sulfate, and basic copper calcium sulfate.

(30) The compositions for controlling harmful bio-organisms according to (27), wherein the organophosphorus compound is at least one member selected from the group consisting of aluminum tris(ethyl phosphonate), O-2,6-dichloro-p-tolyl-O,O-dimethyl phosphorothioate, (R,S)-S-

(R,S)-sec-butyl-O-ethyl-2-oxo-2-thiazolidinyl phosphonothioate, S-benzyl diisopropyl phosphorothioate, O-ethyl diphenyl phosphorodithioate, and ethyl 2-diethoxythiophosphoryloxy-5-methylpyrazolo (1,5-a)pyrimidine-6-carboxylate.

(31) The compositions for controlling harmful bio-organisms according to (27), wherein the organophosphorus compound is aluminum tris(ethyl phosphonate).

(32) The compositions for controlling harmful bio-organisms according to (27), wherein the weight ratio of at least one imidazole compound of formula (I) to the copper compound and/or the organophosphorus compound is 1:2000 to 2000:1.

Preferred embodiments of applying the composition containing active ingredient (a) and activity-enhancing ingredient (c) to harmful bio-organisms are described below for illustrative purposes only but not for limitation.

(1) The compositions containing active ingredient (a) and activity-enhancing ingredient (c) can be applied to harmful bio-organisms in the form of an aqueous dispersion. In this method, the aqueous dispersion is sprayed over the sites where a harmful bio-organism has occurred or is expected to occur, such as foliage of useful plants or soil. The aqueous dispersion is particularly effective for application to foliage. The aqueous dispersion is prepared, for example, by (i) dispersing a preparation of the active ingredient in water and adding thereto the activity-enhancing ingredient; (ii) dispersing a preparation containing the active ingredient and the activity-enhancing ingredient in water; or the method similar to (i) or (ii). The aqueous dispersion to be applied is prepared by using 1 liter of water per 0.1 to 10,000 mg of the compositions for controlling harmful bio-organisms so as to have the active ingredient in a concentration of 0.1 to 10,000 ppm. The aqueous dispersion is sprayed in an amount of 100 to 10,000 l/ha.

(2) The compositions containing active ingredient (a) and activity-enhancing ingredient (c) can be applied in the form of an aqueous suspension in the same manner as for the aqueous dispersion. The concentration of the active ingredient in the aqueous suspension is 0.1 to 10,000 ppm. The aqueous suspension is sprayed in an amount of 100 to 10,000 l/ha.

Test Examples of the compositions for controlling harmful bio-organisms of the present invention in usage as an agricultural or horticultural fungicide are given below for illustrative purposes.

TEST EXAMPLE 1

Test of Curative Effect on Cucumber Downy Mildew

A composition for controlling harmful bio-organisms containing Compound No. 1 and the inorganic phosphorus compound shown in Table 9 below in a concentration of 100 ppm and 2000 ppm, respectively, was prepared by mixing an aqueous suspension concentrate of Compound No. 1 and a 20% wettable powder of the inorganic phosphorus compound. The 20% wettable powder of the inorganic phosphorus compound was prepared in accordance with Reference Formulation Example hereinafter given.

A cucumber (cultivars: Suyo) was cultivated in polyethylene pots (diameter: 7.5 cm). When the plant reached a two-leaf stage, it was inoculated by spraying a spore suspension of fungi of downy mildew (*Pseudoperonospora cubensis*). After 24 hours, 10 ml/pot of the above-prepared composition was sprayed onto the plant by means of a spray gun. For comparison, the same test was carried out by using 10 ml of a composition containing 2000 ppm of the inorganic phosphorus compound and containing no Compound No. 1 or 10 ml of a composition containing 100 ppm of Compound No. 1 and containing no inorganic phosphorus compound. The plant was kept in a chamber set at 22 to 24° C. for 6 days, and the lesion area of the first leaf was measured, from which the disease incidence rate (%) was calculated according to the following formula. The results obtained are shown in Table 9.

Incidence rate (%)=(a/b)×100 wherein a is a lesion area of a treated plant; and b is a lesion area of a control (non-treated plant).

A theoretical incidence rate (%) can be calculated from the following Colby's formula. In cases where an incidence rate of a tested composition is lower than the theoretical one, the tested composition can be the to produce a synergistic effect. In these cases, the theoretical incidence rate (%) is shown in parentheses in Table 9.

Theoretical incidence rate (%)=($X^1$×$Y^1$)/100 wherein $X^1$ is an incidence rate (%) of a plant treated with only Compound No. 1; and $Y^1$ is an incidence rate (%) of a plant treated with only the inorganic phosphorus compound.

TABLE 9

| Curative Effect on Cucumber Downy Mildew (Incidence Rate; %) | | |
|---|---|---|
| Inorganic Phosphorus | Compound No. 1 | |
| Compound, 2000 ppm | 100 ppm | 0 ppm |
| $Na_3PO_4.12H_2O$ | 0 (90.2) | 95 |
| $Al(H_2PO_4)_3$ | 5 (95) | 100 |
| $H_2(PO_3H)$ | 12.5 (71.3) | 75 |
| $Na_2HPO_3.5H_2O$ | 0 (85.5) | 90 |
| $K_2HPO_4$ | 2.5 (90.2) | 95 |
| $Na_2HPO_4$ | 2.5 (95) | 100 |
| none | 95 | 100 (control) |

TEST EXAMPLE 2

Test of Curative Effect on Cucumber Downy Mildew

A composition for controlling harmful bio-organisms containing Compound No. 1 in a prescribed concentration and the inorganic phosphorus compound shown in Table 10 below in a concentration of 250 ppm was prepared by mixing an aqueous suspension concentrate of Compound No. 1 and a 20% wettable powder of the inorganic phosphorus compound. The 20% wettable powder of the inorganic phosphorus compound was prepared in accordance with Reference Formulation Example hereinafter given.

A cucumber (cultivars: Suyo) was cultivated in polyethylene pots (diameter: 7.5 cm). When the plant reached a two-leaf stage, it was inoculated by spraying a spore suspension of fungi of downy mildew (*Pseudoperonospora cubensis*). After 24 hours, 10 ml/pot of the above-prepared composition was sprayed onto the plant by means of a spray gun. For comparison, the same test was carried out by using 10 ml/pot of a composition containing 250 ppm of the inorganic phosphorus compound and containing no Compound No. 1 or 10 ml/pot of a composition containing Compound No. 1 at a prescribed concentration and containing no inorganic phosphorus compound. The plant was kept in a chamber set at 22 to 24° C. for 4 days, and the lesion area of the first leaf was measured, from which the disease incidence rate (%) was calculated according to the following formula. The results obtained are shown in Table 10.

Incidence rate (%)=(a/b)×100 wherein a is a lesion area of a treated plant; and b is a lesion area of a control (non-treated plant).

A theoretical incidence rate (%) can be calculated from the following Colby's formula. In cases where an incidence rate of a tested composition is lower than the theoretical one, the tested composition can be the to produce a synergistic effect. In these cases, the theoretical incidence rate (%) is shown in parentheses in Table 10.

Theoretical incidence rate (%)=$(X^2 \times Y^2)/100$ wherein $X^2$ is an incidence rate (%) of a plant treated with only Compound No. 1; and $Y^2$ is an incidence rate (%) of a plant treated with only the inorganic phosphorus compound.

TABLE 10

Curative Effect on Cucumber Downy Mildew
(Incidence Rate; %)

| Inorganic Phosphorus | Compound No. 1 | | |
|---|---|---|---|
| Compound, 250 ppm | 50 ppm | 12.5 ppm | 0 ppm |
| Na$_3$PO$_4$.12H$_2$O | 0 (77) | 3 (81) | 90 |
| Al(H$_2$PO$_4$)$_3$ | 0 (85) | 0 (90) | 100 |
| H$_2$(PO$_3$H) | 0 (64) | 3 (68) | 75 |
| Na$_2$HPO$_3$.5H$_2$O | 0 (72) | 3 (77) | 85 |
| K$_2$HPO$_4$ | 0 (81) | 5 (86) | 95 |
| Na$_2$HPO$_4$ | 3 (85) | 3 (90) | 100 |
| none | 85 | 90 | 100 (control) |

TEST EXAMPLE 3

Field Test of Effect on Cucumber Downy Mildew

Five cucumber seedlings (cultivars: Tokiwa Kohai Hikari No. 3, P type) in the two-leaf stage were planted in a divided area (3 m² each) of the field located in Kusatsu City, Shiga, Japan on May 10, 1997. A composition containing 50 ppm of Compound No. 1 and 1500 ppm of an inorganic phosphorus compound shown in Table 11 below was sprayed in an amount of 500 ml per area by means of a small-sized spraying machine on June 10 and 17. For comparison, the same field test was carried out by using a composition containing only 1500 ppm of the inorganic phosphorus compound or a composition containing only 50 ppm of Compound No. 1. On June 23, all the leaves were observed to obtain a control index in accordance with the following rating system. The results obtained are shown in Table 11. Artificial infection with a pathogenic fungus was not conducted so that the disease was spontaneous.

| Control Index | Severity of Disease |
|---|---|
| 5 | The lesion area or length is less than 3% of that of a control (non-treated area). |

-continued

| Control Index | Severity of Disease |
|---|---|
| 4 | The lesion area or length is 3% or more and less than 5% of that of the control. |
| 3 | The lesion area or length is 5% or more and less than 10% of that of the control. |
| 2 | The lesion area or length is 10% or more and less than 30% of that of the control. |
| 1 | The lesion area or length is 30% or more of that of the control. |

TABLE 11

Field Test on Cucumber Downy Mildew (Control Index)

| Inorganic Phosphorus | Compound No. 1 | |
|---|---|---|
| Compound, 1500 ppm | 50 ppm | 0 ppm |
| Alexin 95 PS* | 5 | 1 |
| Phytex 200 SL** | 5 | 1 |
| none | 3 | 1 |

Note:
*An aqueous solution having an phosphorous acid concentration of 600 g/l, available from Massō.
**An aqueous solution having a phosphorous acid concentration of 200 g/l, available from Horticura cc).

TEST EXAMPLE 4

Test of Curative Effect on Cucumber Downy Mildew

A cucumber (cultivars: Suyo) was cultivated in polyethylene pots (diameter: 7.5 cm). When the plant reached a two-leaf stage, it was inoculated by spraying a spore suspension of fungi of downy mildew (*Pseudoperonospora cubensis*). After 24 hours, 10 ml of a composition containing the compounds shown in Tables 12 to 19 in respective concentrations shown was sprayed onto the plant by means of a spray gun. The plant was kept in a chamber set at 22 to 24° C. for 6 days, and the lesion area of the first leaf was measured, from which the disease incidence rate (%) was calculated according to the following formula. The results obtained are shown in Tables 12 to 19.

Incidence rate (%)=(a/b)×100 wherein a is a lesion area of a treated plant; and b is a lesion area of a control (non-treated plant).

A theoretical incidence rate (%) can be calculated from the following Colby's formula. In cases where an incidence rate of a tested composition is lower than the theoretical one, the tested composition can be the to produce a synergistic effect. In these cases, the theoretical incidence rate (%) is shown in parentheses in Tables 12 to 19.

Theoretical incidence rate (%) $(X^3 \times Y^3)/100$ wherein $X^3$ is an incidence rate (%) of a plant treated with only Compound No. 1, 2 or 3; and $Y^3$ is an incidence rate (%) of a plant treated with only compound (a) (i.e., methyl (E)-2-{2-[6-(2-cyanophenoxy)pyrimidin-4-yloxy]phenyl}-3-methoxyacrylate), compound (b) (i.e., methyl (E)-methoxyimino[α-(o-tolyloxy)-O-tolyl]acetate), Cymoxanil, Metalaxyl or Dimethomorph.

TABLE 12

Curative Effect on Cucumber Downy Mildew (Incidence Rate; %)

|  | Compound (a) | | |
|---|---|---|---|
| Compound No. 1 | 63 ppm | 2 ppm | 0 ppm |
| 500 ppm | 0 (0.5) | 5 (10) | 10 |
| 125 ppm | 5 | 0 (5) | 5 |
| 31 ppm | 5 | 5 (50) | 50 |
| 8 ppm | 0 (5) | 5 (100) | 100 |
| 0 ppm | 5 | 100 (100) | 100 |

TABLE 13

Curative Effect on Cucumber Downy Mildew (Incidence Rate; %)

|  | Compound (b) | | |
|---|---|---|---|
| Compound No. 1 | 500 ppm | 125 ppm | 0 ppm |
| 500 ppm | 10 | 0 (10) | 10 |
| 125 ppm | 0 (5) | 0 (5) | 5 |
| 31 ppm | 10 (50) | 0 (50) | 50 |
| 8 ppm | 10 (100) | 10 (100) | 100 |
| 0 ppm | 100 | 100 | 100 |

TABLE 14

Curative Effect on Cucumber Downy Mildew (Incidence Rate; %)

|  | Compound (a) | |
|---|---|---|
| Compound No. 3 | 2 ppm | 0 ppm |
| 125 ppm | 5 (10) | 10 |
| 31 ppm | 5 (10) | 10 |
| 8 ppm | 10 (50) | 50 |
| 2 ppm | 50 | 50 |
| 0 ppm | 100 | 100 |

TABLE 15

Curative Effect on Cucumber Downy Mildew (Incidence Rate; %)

|  | Compound (b) | | |
|---|---|---|---|
| Compound No. 3 | 500 ppm | 125 ppm | 0 ppm |
| 125 ppm | 5 (10) | 10 | 10 |
| 31 ppm | 5 (10) | 5 (10) | 10 |
| 8 ppm | 5 (50) | 10 (50) | 50 |
| 2 ppm | 50 | 10 (50) | 50 |
| 0 ppm | 100 | 100 | 100 |

TABLE 16

Curative Effect on Cucumber Downy Mildew (Incidence Rate; %)

| Compound | Cymoxanil | | | |
|---|---|---|---|---|
| No. 1 | 31 ppm | 8 ppm | 2 ppm | 0 ppm |
| 8 ppm | 0 (7) | 15 (70) | 85 | 70 |
| 2 ppm | 2 (10) | 15 (100) | 85 (100) | 100 |
| 0.5 ppm | 10 | 50 (100) | 70 (100) | 100 |
| 0.125 ppm | 7 (10) | 100 | 100 | 100 |
| 0 ppm | 10 | 100 | 100 | 100 |

TABLE 17

Curative Effect on Cucumber Downy Mildew (Incidence Rate; %)

|  | Cymoxanil | |
|---|---|---|
| Compound No. 2 | 31 ppm | 0 ppm |
| 125 ppm | 5 (7) | 10 |
| 31 ppm | 5 (7) | 10 |
| 8 ppm | 5 (35) | 50 |
| 2 ppm | 5 (70) | 100 |
| 0 ppm | 70 | 100 |

TABLE 18

Curative Effect on Cucumber Downy Mildew (Incidence Rate; %)

|  | Metalaxyl | | |
|---|---|---|---|
| Compound No. 1 | 2 ppm | 0.5 ppm | 0 ppm |
| 8 ppm | 20 (42) | 10 (70) | 70 |
| 2 ppm | 7 (60) | 70 (100) | 100 |
| 0.5 ppm | 35 (60) | 85 (100) | 100 |
| 0.125 ppm | 70 | 100 | 100 |
| 0 ppm | 60 | 100 | 100 |

TABLE 19

Curative Effect on Cucumber Downy Mildew (Incidence Rate; %)

|  | Dimethomorph | | |
|---|---|---|---|
| Compound No. 1 | 31 ppm | 8 ppm | 0 ppm |
| 8 ppm | 0 (35) | 4 (42) | 70 |
| 2 ppm | 4 (50) | 50 (60) | 100 |
| 0.5 ppm | 20 (50) | 85 | 100 |
| 0 ppm | 50 | 60 | 100 |

TEST EXAMPLE 5

Test of Curative Effect on Cucumber Downy Mildew

A cucumber (cultivars: Suyo) was cultivated in polyethylene pots (diameter: 7.5 cm). When the plant reached a two-leaf stage, it was inoculated by spraying a spore suspension of fungi of downy mildew (*Pseudoperonospora cubensis*). After 18 hours, 20 ml of a composition containing Compound No. 1 and compound (c) (3-anilino-5-methyl-5-(4-phenoxyphenyl)-1,3-oxazolidine-2,4-dione) in respective concentrations shown in Table 20 was sprayed on two seedlings by means of a spray gun. The plants were kept in a chamber set at 22 to 24° C. for 5 days, and the average lesion area of the two seedlings was obtained, from which the disease incidence rate (%) was calculated in the same manner as in Test Example 1. The results obtained are shown in Table 20.

A theoretical incidence rate (%) can be calculated from the following Colby's formula. In cases where an incidence rate of a tested composition is lower than the theoretical one, the tested composition can be the to produce a synergistic effect. In these cases, the theoretical incidence rate (%) is shown in parenthesis in Table 20.

Theoretical incidence rate (%)=$(X^4 \times Y^4)/100$ wherein $X^4$ is an incidence rate (%) of a plant treated with only Compound No. 1; and $Y^4$ is an incidence rate (%) of a plant treated with only compound (c).

TABLE 20

Curative Effect on Cucumber Downy Mildew (Incidence Rate; %)

| Compound No. 1 | Compound (c) | | | |
|---|---|---|---|---|
| | 800 ppm | 400 ppm | 200 ppm | 0 ppm |
| 200 ppm | 0 (4) | 0 (13) | 0 (48) | 87 |
| 100 ppm | 0 (5) | 0 (14) | 0 (52) | 95 |
| 50 ppm | 0 (5) | 0 (14) | 0 (52) | 95 |
| 0 ppm | 5 | 15 | 55 | 100 |

TEST EXAMPLE 6

Test of Curative Effect on Tomato Late Blight

A tomato (cultivar: Ponderosa) was cultivated in polyethylene pots (diameter: 7.5 cm). When the plant reached a four-leaf stage, it was inoculated by spraying a zoosporangium suspension of fungi of late blight (*Phytophthora infestans*). After 6 hours, 10 ml/pot of a composition containing Compound No. 1 and Cymoxanil, Metalaxyl or Dimethomorph in the respective concentrations shown in Tables 21 to 23 was sprayed on the plant by means of a spray gun. The plant was kept in a chamber set at 22 to 24° C. for 3 to 5 days, and the lesion area was measured, from which the disease incidence rate (%) was calculated in the same manner as in Test Example 1. The results obtained are shown in Tables 21 to 23.

A theoretical incidence rate (%) can be calculated from the following Colby's formula. In cases where an incidence rate of a tested composition is lower than the theoretical one, the tested composition can be the to produce a synergistic effect. In these cases, the theoretical incidence rate (%) is shown in parentheses in Tables 21 to 23.

Theoretical incidence rate (%)=$(X^5 \times Y^5)/100$ wherein $X^5$ is an incidence rate (%) of a plant treated with only Compound No. 1; and $Y^5$ is an incidence rate (%) of a plant treated with only Cymoxanil, Metalaxyl or Dimethomorph.

TABLE 21

Curative Effect on Tomato Late Blight (Incidence Rate; %)

| Compound No. 1 | Cymoxanil | | |
|---|---|---|---|
| | 2 ppm | 0.5 ppm | 0 ppm |
| 500 ppm | 0 (10) | 4 (10) | 10 |
| 125 ppm | 70 (85) | 60 (85) | 85 |
| 31 ppm | 70 (100) | 85 (100) | 100 |
| 8 ppm | 85 (100) | 100 | 100 |
| 0 ppm | 100 | 100 | 100 |

TABLE 22

Curative Effect on Tomato Late Blight (Incidence Rate; %)

| Compound No. 1 | Metalaxyl | | | |
|---|---|---|---|---|
| | 8 ppm | 2 ppm | 0.5 ppm | 0 ppm |
| 500 ppm | 2 | 2 | 0 (7) | 10 |
| 125 ppm | 0 (13) | 2 (13) | 10 (59) | 85 |
| 31 ppm | 7 (15) | 7 (15) | 20 (70) | 100 |
| 8 ppm | 7 (15) | 10 (15) | 60 (70) | 100 |
| 0 ppm | 15 | 15 | 70 | 100 |

TABLE 23

Curative Effect on Tomato Late Blight (Incidence Rate; %)

| Compound No. 1 | Dimethomorph | | |
|---|---|---|---|
| | 31 ppm | 8 ppm | 0 ppm |
| 500 ppm | 0 (8.5) | 0 (10) | 10 |
| 125 ppm | 4 (72) | 20 (85) | 85 |
| 31 ppm | 60 (85) | 70 (100) | 100 |
| 8 ppm | 30 (85) | 100 | 100 |
| 0 ppm | 85 | 100 | 100 |

TEST EXAMPLE 7

Field Test on Cucumber Downy Mildew

Seven cucumber seedlings (cultivar: Tokiwa Kohai Hikari No. 3, P type) were planted in a divided area 5 m² each) of the field located in Kusatsu City, Shiga, Japan on May 9, 1995. A composition containing Compound No. 1 and Chlorothalonil in the respective concentrations shown in Table 24 below was sprayed over the plants in an amount of 500 to 750 ml per area by means of a small-sized spraying machine on May 30 and June 6. On June 14, all the leaves were observed to obtain a control index in accordance with the following rating system. The results obtained are shown in Table 24. Artificial infection with a pathogenic fungus was not conducted so that the disease was spontaneous.

| Control Index | Severity of Disease |
|---|---|
| 5 | The lesion area or length is less than 7% of that of a control (non-treated area). |
| 4 | The lesion area or length is 7% or more and less than 10% of that of the control. |
| 3 | The lesion area or length is 10% or more and less than 20% of that of the control. |
| 2 | The lesion area or length is 20% or more and less than 30% of that of the control. |
| 1 | The lesion area or length is 30% or more of that of the control. |

TABLE 24

Field Test on Cucumber Downy Mildew
(Control Index)

| Compound No. 1 | Chlorothalonil | |
| --- | --- | --- |
| | 400 ppm | 0 ppm |
| 12.5 ppm | 5 | 3 |
| 0 ppm | 1 | 1 |

TEST EXAMPLE 8

Test of Preventive Effect on Cucumber Downy Mildew

A cucumber (cultivar: Suyo) was cultivated in polyethylene pots (diameter: 7.5 cm). When the plant reached a two-leaf stage, 10 ml of a composition containing Compound No. 1 and Deutch Bordeaux A (trade name of copper oxychloride wettable powder produced by Hokko Chemical Industry Co., Ltd.) in respective concentrations shown in Table 25 below was sprayed on the seedling by means of a spray gun. After 24 hours, it was inoculated by spraying a spore suspension of fungi of dawny mildew (*Pseudoperonospora cubensis*). The plant was kept in a chamber set at 22 to 24° C. for 6 days, and the lesion area of the first leaf was measured, from which the disease incidence rate (%) was calculated according to the following formula. The results obtained are shown in Table 25.

Incidence rate (%)=(a/b)×100 wherein a is a lesion area of a treated plant; and b is a lesion area of a control (non-treated plant).

A theoretical incidence rate (%) can be calculated from the following Colby's formula. In cases where an incidence rate of a tested composition is lower than the theoretical one, the tested composition can be the to produce a synergistic effect. In these cases, the theoretical incidence rate (%) is shown in parentheses in Table 25.

Theoretical incidence rate (%)=($X^6 \times Y^6$)/100 wherein $X^6$ is an incidence rate (%) of a plant treated with only Compound No. 1; and $Y^6$ is an incidence rate (%) of a plant treated with only Duitch Bordeaux A.

TABLE 25

Preventive Effect on Cucumber Downy Mildew
(Incidence Rate; %)

| Compound No. 1 | Duitch Bordeaux A | |
| --- | --- | --- |
| | 50 ppm | 0 ppm |
| 0.2 ppm | 0 (7) | 7 |
| 0.025 ppm | 70 (100) | 100 |
| 0 ppm | 100 | 100 |

TEST EXAMPLE 9

Test of Preventive Effect on Tomato Late Blight

A tomato (cultivar: Ponderosa) was cultivated in polyethylene pots (diameter: 7.5 cm). When the plant reached a four-leaf stage, 10 ml of a composition containing Compound No. 1 and Kocide Bordeaux (trade name of a cupric hydroxide wettable powder produced by Griffin) or Duitch Bordeaux A (trade name of copper oxychloride wettable powder produced by Hokko Chemical Industry Co., Ltd.) in the respective concentrations shown in Tables 26 and 27 below was sprayed on the seedling by means of a spray gun. After 24 hours, it was inoculated by spraying a zoosporangium suspension of fungi of late blight (*Phytophthora infestans*). The plant was kept in a chamber set at 22 to 24° C. for 3 days, and the lesion area was measured, from which the disease incidence rate (%) was calculated in the same manner as in Test Example 1. The results obtained are shown in Tables 26 and 27.

A theoretical incidence rate (%) can be calculated from the following Colby's formula. In cases where an incidence rate of a tested composition is lower than the theoretical one, the tested composition can be the to produce a synergistic effect. In these cases, the theoretical incidence rate (%) is shown in parentheses in Tables 26 and 27.

Theoretical incidence rate (%)=($X^7 \times Y^7$)/100 wherein $X^7$ is an incidence rate (%) of a plant treated with only Compound No. 1; and $Y^7$ is an incidence rate (%) of a plant treated with only Kocide Bordeaux or Deutch Bordeaux A.

TABLE 26

Preventive Effect on Tomato Late Blight
(Incidence Rate; %)

| Compound No. 1 | Kocide Bordeaux | |
| --- | --- | --- |
| | 50 ppm | 0 ppm |
| 0.8 ppm | 9 (47) | 47 |
| 0.4 ppm | 37 (50) | 50 |
| 0 ppm | 100 | 100 |

TABLE 27

Preventive Effect on Tomato Late Blight
(Incidence Rate; %)

| Compound No. 1 | Deutch Bordeaux A | |
| --- | --- | --- |
| | 200 ppm | 0 ppm |
| 3 ppm | 0 (31) | 31 |
| 1.5 ppm | 3 (37) | 37 |
| 0 ppm | 100 | 100 |

TEST EXAMPLE 10

Test of Curative Effect on Cucumber Downy Mildew

A cucumber (cultivar: Suyo) was cultivated in polyethylene pots (diameter: 7.5 cm). When the plant reached a two-leaf stage, it was inoculated by spraying a spore suspension of fungi of downy mildew (*Pseudoperonospora cubensis*). After 24 hours, 10 ml of a composition containing Compound No. 1 and aluminum tris(ethyl phosphonate) (Fosetyl-aluminum) in the respective concentrations shown in Table 28 was sprayed onto the plant by means of a spray gun. The plant was kept in a chamber set at 22 to 24° C. for 6 days, and the lesion area of the first leaf was measured, from which the disease incidence rate (%) was calculated in the same manner as in Test Example 1. The results obtained are shown in Table 28.

A theoretical incidence rate (%) can be calculated from the following Colby's formula. In cases where an incidence rate of a tested composition is lower than the theoretical one, the tested composition can be the to produce a synergistic effect. In these cases, the theoretical incidence rate (%) is shown in parentheses in Table 28.

Theoretical incidence rate (%)=$(X^8 \times Y^8)/100$ wherein $X^8$ is an incidence rate (%) of a plant treated with only Compound No. 1; and $Y^8$ is an incidence rate (%) of a plant treated with only Fosetyl-aluminum.

TABLE 28

Curative Effect on Cucumber Downy Mildew (Incidence Rate; %)

| Compound No. 1 | Fosetyl-Aluminum | | |
|---|---|---|---|
| | 2000 ppm | 500 ppm | 0 ppm |
| 50 ppm | 12.5 (48.8) | 40 (55.3) | 65 |
| 0 ppm | 75 | 85 | 100 |

TEST EXAMPLE 11

Test of Curative Effect on Cucumber Downy Mildew

Preparation of Aqueous Dispersion:

A spreader (activity-enhancing ingredient) shown in Table 29 below was 500-fold or 1000-fold diluted with water, and Compound No. 1 was added thereto in a concentration of 100 ppm or 12.5 ppm to prepare an aqueous dispersion. For comparison, an aqueous dispersion containing 100 ppm or 12.5 ppm of Compound No. 1 and containing no activity-enhancing ingredient was prepared in the same manner.

Test Method and Results:

A cucumber (cultivar: Suyo) was cultivated in polyethylene pots (diameter: 7.5 cm). When the plant reached a two-leaf stage, it was inoculated by spraying a spore suspension of fungi of downy mildew (*Pseudoperonospora cubensis*). After 15 to 24 hours, the aqueous dispersion was sprayed over the plant with a spray gun in an amount of 20 ml per 0.25 m². The plant was kept in a chamber set at 22 to 24° C. for 4 to 6 days, and the lesion area of the first leaf was measured to obtain a control index in accordance with the following rating system. The results obtained are shown in Table 29.

| Control Index | Severity of Disease |
|---|---|
| 4 | The lesion area or length is less than 20% of that of a control (non-treated plant). |
| 3 | The lesion area or length is 20% or more and less than 40% of that of the control. |
| 2 | The lesion area or length is 40% or more and less than 60% of that of the control. |
| 1 | The lesion area or length is 60% or more of that of the control. |

TABLE 29

| | Activity-enhancing ingredient (Spreader) | Control Index Conc. of Compound No. 1 | |
|---|---|---|---|
| | Dilution | (ppm) | |
| No. | Rate | 100 | 12.5 |
| 1 | 500-fold | — | 4 |
| 2 | 500-fold | — | 4 |
| 3 | 500-fold | — | 4 |
| 4 | 500-fold | 4 | 3 |
| 5 | 500-fold | 4 | 3 |
| 6 | 500-fold | 4 | 2 |
| 7 | 500-fold | 4 | 4 |
| 8 | 500-fold | 4 | 4 |
| 9 | 500-fold | — | 4 |
| 10 | 1000-fold | 4 | 3 |
| 11 | 500-fold | — | 4 |
| 12 | 500-fold | — | 4 |
| 13 | 500-fold | — | 4 |
| 14 | 500-fold | — | 4 |
| 15 | 500-fold | — | 4 |
| 16 | 500-fold | — | 4 |
| 17 | 500-fold | — | 4 |
| 18 | 500-fold | — | 4 |
| 19 | 500-fold | — | 4 |
| 20 | 500-fold | — | 4 |
| 21 | 500-fold | 3 | — |
| 22 | 500-fold | — | 4 |
| 23 | 500-fold | — | 4 |
| 25 | 500-fold | — | 4 |
| 26 | 500-fold | 4 | 4 |
| 27 | 500-fold | 4 | 4 |
| 28 | 500-fold | — | 4 |
| 29 | 500-fold | — | 4 |
| 30 | 500-fold | — | 4 |
| 31 | 500-fold | — | 4 |
| 32 | 500-fold | — | 4 |
| 33 | 500-fold | — | 4 |
| 34 | 500-fold | — | 4 |
| 35 | 500-fold | — | 4 |
| 36 | 500-fold | 4 | 3 |
| 37 | 500-fold | 4 | 4 |
| 38 | 500-fold | 4 | 4 |
| 40 | 500-fold | — | 4 |
| 41 | 500-fold | — | 4 |
| 42 | 500-fold | — | 4 |
| 43 | 500-fold | — | 4 |
| 44 | 500-fold | — | 4 |
| 45 | 500-fold | 4 | 3 |
| 46 | 500-fold | — | 4 |
| 47 | 500-fold | — | 4 |
| 48 | 500-fold | 4 | 4 |
| 49 | 500-fold | 4 | 3 |
| 50 | 500-fold | 4 | 4 |
| 51 | 500-fold | 4 | 4 |
| 52 | 500-fold | 4 | 4 |
| 53 | 500-fold | 4 | 4 |
| 54 | 500-fold | 4 | 4 |
| 55 | 500-fold | 4 | 4 |
| 56 | 500-fold | — | 4 |
| 57 | 500-fold | 4 | 4 |
| 59 | 500-fold | 4 | 4 |
| 60 | 500-fold | 4 | 4 |
| 61 | 500-fold | — | 4 |
| 62 | 500-fold | — | 4 |
| 63 | 500-fold | — | 4 |
| 64 | 500-fold | — | 4 |
| 65 | 500-fold | — | 4 |
| 66 | 500-fold | — | 4 |
| 67 | 500-fold | — | 4 |
| 68 | 1000-fold | — | 4 |
| 70 | 500-fold | — | 4 |
| 71 | 500-fold | — | 4 |
| 72 | 500-fold | 4 | 4 |
| 73 | 500-fold | — | 3 |

TABLE 29-continued

| No. | Activity-enhancing ingredient (Spreader) Dilution Rate | Control Index Conc. of Compound No. 1 (ppm) 100 | 12.5 |
|---|---|---|---|
| 74 | 500-fold | — | 4 |
| 75 | 500-fold | — | 4 |
| 76 | 500-fold | 4 | 4 |
| 77 | 500-fold | 4 | 4 |
| 78 | 500-fold | — | 4 |
| 79 | 500-fold | — | 4 |
| 80 | 500-fold | — | 4 |
| 81 | 500-fold | — | 4 |
| 82 | 500-fold | — | 4 |
| 83 | 500-fold | — | 4 |
| 84 | 500-fold | — | 4 |
| 85 | 500-fold | — | 4 |
| 86 | 500-fold | — | 4 |
| 87 | 500-fold | — | 4 |
|  | none | 1 | 1 |

TEST EXAMPLE 12

Test of Curative Effect on Tomato Late Blight

Preparation of Aqueous Dispersion:

A spreader (activity-enhancing ingredient) shown in Table 30 below was 500-fold diluted with water, and Compound No. 1 was added thereto in a concentration of 400 ppm or 12.5 ppm to prepare an aqueous dispersion.

For comparison, an aqueous dispersion was prepared in the same manner, except for using a sorbitan fatty acid ester surface active agent shown in Table 30 below (comparative spreader A, B or C) as a spreader and adding Compound No. 1 in a concentration of 400 ppm. For further comparison, an aqueous dispersion containing 400 ppm or 12.5 ppm of Compound No. 1 and containing no activity-enhancing ingredient was prepared in the same manner.

TABLE 30

| Comparative Spreader | Kind | Designation | Trade Name (Manufacturer) |
|---|---|---|---|
| A | polyoxyethylene hexitan fatty acid ester | polyoxyethylene hexitan fatty acid ester | APPLAUCH ® (Kao Corporation) |
| B | polyoxyethylene hexitan fatty acid ester | polyoxyethylene hexitan fatty acid ester 50% | Alsoap 30 (Sankei Chemical Co., Ltd., Takeda Chemical Industries, Ltd.) |
| C | polyoxyethylene sorbitan fatty acid ester | oxysorbic polyoxyethylene sorbitan monolaurate | Tween 20 (Wako Pure Chemical Industries, Ltd.) |

Test Method and Results:

A tomato (cultivar: Ponderosa) was cultivated in polyethylene pots (diameter: 7.5 cm). When the plant reached a four-leaf stage, it was inoculated by spraying a zoosporangium suspension of fungi of late blight (*Phytophthora infestans*). After 4 hours, the aqueous dispersion above prepared was sprayed over the plant with a spray gun in an amount of 20 ml per 0.25 m After the plant was kept in a chamber set at 22 to 24° C. for 3 days, the lesion area was measured, from which a control index was obtained in accordance with the same rating system as in Test Example 11. The results obtained are shown in Table 31.

TABLE 31

Curative Effect on Tomato Late Blight (Control Index)

| No. | Activity-enhancing ingredient (Spreader) Dilution Rate | Control Index Conc. of Compound No. 1 (ppm) 400 | 12.5 |
|---|---|---|---|
| 7 | 500-fold | 3 | — |
| 19 | 500-fold | 4 | — |
| 22 | 500-fold | 3 | — |
| 23 | 500-fold | — | 4 |
| 25 | 500-fold | — | 3 |
| 27 | 500-fold | 3 | — |
| 35 | 500-fold | 4 | — |
| 39 | 500-fold | — | 4 |
| 42 | 500-fold | — | 4 |
| 43 | 500-fold | — | 4 |
| 46 | 500-fold | — | 3 |
| 55 | 500-fold | 3 | — |
| 61 | 500-fold | 3 | — |
| 67 | 500-fold | 4 | — |
| 76 | 500-fold | 3 | — |
| 88 | 500-fold | — | 3 |
| 90 | 500-fold | — | 4 |
| Comparative |  |  |  |
| A | 500-fold | 2 | — |
| B | 500-fold | 2 | — |
| C | 500-fold | 2 | — |
|  | none | 1 | 1 |

TEST EXAMPLE 13

Test of Curative Effect on Tomato Late Blight

Preparation of Aqueous Dispersion:

A spreader (activity-enhancing ingredient) shown in Table 32 below was 2000-fold diluted with water, and Compound No. 1 was added thereto in a concentration of 100 ppm to prepare an aqueous dispersion. For comparison, an aqueous dispersion containing 100 ppm of Compound No. 1 and containing no activity-enhancing ingredient was prepared in the same manner.

Test Method and Results:

A tomato (cultivar: Ponderosa) was cultivated in polyethylene pots (diameter: 7.5 cm). When the plant reached a four-leaf stage, it was inoculated by spraying a zoosporangium suspension of fungi of late blight (*Phytophthora infestans*). After 4 hours, the aqueous dispersion above prepared was sprayed over the plant with a spray gun in an amount of 20 ml per 0.25 m². After the plant was kept in a chamber set at 22 to 24° C. for 3 days, the lesion area was measured, from which a control index was obtained in accordance with the same rating system as in Test Example 11. The results obtained are shown in Table 32.

TABLE 32

Curative Effect on Tomato Late Blight (Control Index)

| Activity-enhancing ingredient | | | | | No Activity-enhancing ingredient |
|---|---|---|---|---|---|
| Spreader No. | | | | | |
| 23 | 24 | 39 | 88 | 90 | |
| Control Index 4 | 4 | 4 | 4 | 4 | 2 |

TEST EXAMPLE 14

Test of Preventive Effect on Tomato Late Blight

Preparation of Aqueous Dispersion:

Spreader No. 58 or 91 (activity-enhancing ingredient) was 500-fold diluted with water, and Compound No. 1 was added thereto in a prescribed concentration to prepare an aqueous dispersion. For comparison, an aqueous dispersion containing the same concentration of Compound No. 1 and containing no activity-enhancing ingredient was prepared in the same manner.

Test Method and Results:

A tomato (cultivar: Ponderosa) was cultivated in polyethylene pots (diameter: 7.5 cm). When the plant reached a four-leaf stage, the aqueous dispersion above prepared was sprayed over the plant with a spray gun in an amount of 20 ml per 0.25 m². After 24 hours from the spray treatment, a zoosporangium suspension of fungi of late blight (*Phytophthora infestans*) was sprayed for inoculation, and the plant was kept in a chamber set at 22 to 24° C. for 3 days. The lesion area was measured, from which a control index was obtained in accordance with the same rating system as in Test Example 11. The results obtained are shown in Table 33.

TABLE 33

Preventive Effect on Tomato Late Blight (Control Index)

| Compound No. 1 | Activity-enhancing ingredient | | |
|---|---|---|---|
| | Spreader No. 58 (500-fold diluted) | Spreader No. 91 (500-fold diluted) | None |
| 1.6 ppm | 4 | 4 | 3 |
| 0.8 ppm | 4 | 4 | 1 |
| 0.4 ppm | 1 | 3 | 1 |

TEST EXAMPLE 15

Test of Curative Effect on Cucumber Downy Mildew

Preparation of Aqueous Dispersion:

A spreader (activity-enhancing ingredient) shown in Table 34 below was 500-fold or 2000-fold diluted with water, and Compound No. 1 was added thereto in a concentration of 12.5 ppm to prepare an aqueous dispersion. For comparison, an aqueous dispersion containing 12.5 ppm of Compound No. 1 and containing no activity-enhancing ingredient was prepared in the same manner.

Test Method and Results:

A cucumber (cultivar: Suyo) was cultivated in polyethylene pots (diameter: 7.5 cm). When the plant reached a two-leaf stage, it was inoculated by spraying a spore suspension of fungi of downy mildew (*Pseudoperonospora cubensis*) After 15 to 24 hours, the aqueous dispersion was sprayed over the plant with a spray gun in an amount of 20 ml per 0.25 m². The plant was kept in a chamber set at 22 to 24° C. for 5 days, and the lesion area of the first leaf was measured to obtain the lesion-free area ratio (%). The results obtained are shown in Table 34.

TABLE 34

Curative Effect on Cucumber Downy Mildew (Lesion-free Area Ratio; %)

| Dilution Ratio of Activity-enhancing ingredient | Spreader No. | | | | | | |
|---|---|---|---|---|---|---|---|
| | 23 | 24 | 39 | 88 | 89 | 90 | none |
| 500-fold | 100 | 100 | 100 | 95 | 90 | 100 | 65 |
| 2000-fold | 100 | 100 | 100 | 83 | — | 95 | |

(note: all parts on the following Formulation Examples 1-14 and Reference Formulation Example are indicated by weight.)

FORMULATION EXAMPLE 1

| (1) Compound No. 1 | 5 parts (by weight, hereinafter the same) |
|---|---|
| (2) Dipotassium hydrogenphosphate | 7 parts |
| (3) Diatomaceous earth | 82 parts |
| (4) Dialkyl sulfosuccinate | 2 parts |
| (5) Polyoxyethylene alkylphenyl ether sulfate | 4 parts |

The above components were mixed uniformly to obtain a wettable powder.

FORMULATION EXAMPLE 2

| (1) Compound No. 1 | 5 parts |
|---|---|
| (2) Sodium tertiary phosphate dodecahydrate | 16 parts |
| (3) Diatomaceous earth | 73 parts |
| (4) Dialkyl sulfosuccinate | 2 parts |
| (5) Polyoxyethylene alkylphenyl ether sulfate | 4 parts |

The above components were mixed uniformly to obtain a wettable powder.

FORMULATION EXAMPLE 3

| (1) Compound No. 1 | 5 parts |
|---|---|
| (2) Dipotassium hydrogenphosphate | 18 parts |
| (3) Kerosene | 63 parts |
| (4) Dialkyl sulfosuccinate | 2 parts |
| (5) Mixture of polyoxyethylene phenylphenol derivative and polyoxyethylene sorbitan alkylate | 12 parts |

The above components were mixed uniformly and finely ground to obtain a suspension concentrate.

FORMULATION EXAMPLE 4

| | | |
|---|---|---|
| (1) | Kaolin | 78 parts |
| (2) | Sodium β-naphthalenesulfonate-formaldehyde condensate | 2 parts |
| (3) | Polyoxyethylene alkylaryl sulfate | 5 parts |
| (4) | Hydrated amorphous silicon dioxide | 15 parts |

A mixture of the above components, dipotassium hydrogenphosphate, and Compound No. 1 were mixed at a weight ratio of 79:20:1 to obtain a wettable powder.

FORMULATION EXAMPLE 5

| | | |
|---|---|---|
| (1) | Kaolin | 78 parts |
| (2) | Sodium β-naphthalenesulfonate-formaldehyde condensate | 2 parts |
| (3) | Polyoxyethylene alkylaryl sulfate | 5 parts |
| (4) | Hydrated amorphous silicon dioxide | 15 parts |

A mixture of the above components, Compound No. 1, and Metalaxyl were mixed at a weight ratio of 8:1:1 to obtain a wettable powder.

FORMULATION EXAMPLE 6

| | | |
|---|---|---|
| (1) | Compound No. 2 | 0.5 part |
| (2) | Metalaxyl | 0.5 part |
| (3) | Bentonite | 20 parts |
| (4) | Kaolin | 74 parts |
| (5) | Sodium lignin sulfonate | 5 parts |

The above components were mixed together with an adequate amount of water enough for granulation, followed by granulation to obtain granules.

FORMULATION EXAMPLE 7

| | | |
|---|---|---|
| (1) | Compound No. 3 | 0.25 part |
| (2) | Metalaxyl | 0.25 part |
| (3) | Calcium carbonate | 99.0 parts |
| (4) | Lower alcohol phosphate | 0.5 part |

The above components were mixed uniformly to obtain a dust.

FORMULATION EXAMPLE 8

| | | |
|---|---|---|
| (1) | Kaolin | 78 parts |
| (2) | Sodium β-naphthalenesulfonate-formaldehyde condensate | 2 parts |
| (3) | Polyoxyethylene alkylaryl sulfate | 5 parts |
| (4) | Hydrated amorphous silicon dioxide | 15 parts |

A mixture of the above components, Compound No. 1, and Kocide Bordeaux (trade name) were mixed at a weight ratio of 0.8:76.8:22.4 to obtain a wettable powder.

FORMULATION EXAMPLE 9

| | | |
|---|---|---|
| (1) | Kaolin | 78 parts |
| (2) | Sodium β-naphthalenesulfonate-formaldehyde condensate | 2 parts |
| (3) | Polyoxyethylene alkylaryl sulfate | 5 parts |
| (4) | Hydrated amorphous silicon dioxide | 15 parts |

A mixture of the above components, Compound No. 1, and Duitch Bordeaux A (trade name) were mixed at weight ratio of 5:67.2:27.8 to obtain a wettable powder.

FORMULATION EXAMPLE 10

| | | |
|---|---|---|
| (1) | Compound No. 1 | 0.25 part |
| (2) | Sanpun Bordeaux Dust DL (trade name, produced by Dai-ichi Noyaku K.K. and Hokko Chemical Industry Co., Ltd.) | 0.25 part |
| (3) | Sodium carbonate | 99.0 parts |
| (4) | Lower alcohol phosphate | 0.5 part |

The above components were mixed uniformly to obtain a dust.

FORMULATION EXAMPLE 11

| | | |
|---|---|---|
| (1) | Compound No. 1 | 0.5 part |
| (2) | Sanpun Bordeaux Dust DL (trade name, produced by Dai-ichi Noyaku K.K. and Hokko Chemical Industry Co., Ltd.) | 0.5 part |
| (3) | Bentonite | 20 parts |
| (4) | Kaolin | 74 parts |
| (5) | Sodium lignin sulfonate | 5 parts |

The above components were mixed together with an adequate amount of water enough for granulation, followed by granulation to obtain granules.

FORMULATION EXAMPLE 12

| | | |
|---|---|---|
| (1) | Compound No. 1 | 5 parts |
| (2) | Aluminum tris(ethyl phosphonate) (Fosetyl-aluminum) | 5 parts |
| (3) | Diatomaceous earth | 84 parts |
| (4) | Calcium lignin sulfonate | 2 parts |
| (5) | Dialkyl sulfosuccinate | 4 parts |

The above components were mixed uniformly to obtain a wettable powder.

FORMULATION EXAMPLE 13

| | |
|---|---|
| (1) Compound No. 1 (active ingredient) | 11.1 parts |
| (2) Dispersant SOPROPHOR FLK (trade name, produced by RHôNE-POULENC) | 1.1 part |
| (3) Dispersing and wetting agent Supragil MNS/90 (trade name) | 1.1 part |
| (4) Dispersing and suspending agent Vegum | 1.7 parts |
| (5) Urea (acting as an antifreezing agent) | 11.1 parts |
| (6) Antifoaming agent SM5572F (trade name) | 0.1 part |
| (7) Distilled water | 73.8 parts |

The above components (1) to (7) were mixed and wet ground until the active ingredient had an average particle size of 2 μm to prepare a suspension. To 90 parts of the resulting suspension was added 10 parts of an activity-enhancing ingredient, followed by mixing by shaking to prepare an aqueous suspension concentrate.

FORMULATION EXAMPLE 14

| | |
|---|---|
| (1) Compound No. 1 (active ingredient) | 10.0 parts |
| (2) Dispersant SOPROPHOR FLK (trade name, produced by PHôNE-POULENC) | 1.0 part |
| (3) Dispersing and wetting agent Supragil MNS/90 (trade name) | 1.0 part |
| (4) Dispersing and suspending agent Vegum | 1.5 parts |
| (5) Urea (acting as an antifreezing agent) | 10.0 parts |
| (6) Antifoaming agent SM5572F (trade name) | 0.1 part |
| (7) Distilled water | 66.4 parts |
| (8) Activity-enhancing ingredient | 10.0 parts |

The above components (1) to (8) were mixed and wet ground until the active ingredient had an average particle size of 2 μm to prepare an aqueous suspension concentrate.

REFERENCE FORMULATION EXAMPLE

| | |
|---|---|
| (1) Kaolin | 78 parts |
| (2) Sodium β-naphthalenesulfonate-formaldehyde condensate | 2 parts |
| (3) Polyoxyethylene alkylaryl sulfate | 5 parts |
| (4) Hydrated amorphous silicon dioxide | 15 parts |

A mixture of the above components and an inorganic phosphorous compound at a weight ratio of 4:1 to prepare a 20% wettable powder of the inorganic phosphorous compound.

INDUSTRIAL APPLICABILITY

The compositions for controlling harmful bio-organisms according to the present invention have high curative and/or preventive effects on crop plants suffering from plant diseases caused by harmful bio-organisms and can control the harmful bio-organisms. In particular, the compositions containing the activity-enhancing ingredient exhibit enhanced curative effects so that the amount of the active ingredient can be reduced.

While the invention has been described in detail and with reference to specific embodiments thereof, it will be apparent to one skilled in the art that various changes and modifications can be made therein without departing from the spirit and scope thereof.

The invention claimed is:

1. A composition for controlling a fungal disease which is applied to a plant in need of said controlling of said disease in an amount effective to produce a synergistic effect, which comprises
   (a) at least one imidazole compound represented by formula (I):

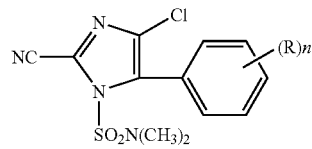

(I)

wherein R represents a lower alkyl group or a lower alkoxy group; and n represents an integer of 1 to 5, as an active ingredient, and (b) at least one fungicide for Phycomycetes which is at least one compound selected from the group consisting of:

methyl (E)-2-{2-[6-(2-cyanophenoxy)pyrimidin-4-yloxy]phenyl}-3-methoxyacrylate, methyl (E)-methoxyimino[α-(o-tolyloxy)-O-tolyl]acetate, 3-anilino-5-methyl-5-(4-phenoxyphenyl)-1,3-oxazolidine-2,4-dione, methyl N-(2-methoxyacetyl)-N-(2,6-xylyl)-DL-alaninate, (E, Z)-4-[3-(4-chlorophenyl)-3-(3,4-dimethoxyphenyl)acrylolyl]morpholine, and an inorganic copper fungicide as an active ingredient.

2. The composition according to claim 1, wherein the imidazole compound and the fungicide are at a weight ratio of 1:1,000 to 10,000:1.

3. The compound according to claim 1, wherein the imidazole compound and the fungicide are at a weight ratio of 1:100 to 1,000:1.

* * * * *